United States Patent
Sato et al.

(10) Patent No.: US 8,568,814 B2
(45) Date of Patent: Oct. 29, 2013

(54) LANTHIONINE DERIVATIVES

(75) Inventors: Seiichi Sato, Kawasaki (JP); Fumie Futaki, Kawasaki (JP); Reiko Yasuda, Kawasaki (JP); Sachise Eto, Kawasaki (JP); Yumiko Suzuki, Kawasaki (JP); Takaho Tajima, Kawasaki (JP); Yuzuru Eto, Kawasaki (JP); Yuki Tahara, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/533,469

(22) Filed: Jun. 26, 2012

(65) Prior Publication Data

US 2012/0282386 A1 Nov. 8, 2012

Related U.S. Application Data

(63) Continuation of application No. PCT/JP2010/073720, filed on Dec. 28, 2010.

(30) Foreign Application Priority Data

Dec. 28, 2009 (JP) ................................. 2009-298010

(51) Int. Cl.
*A23L 1/226* (2006.01)
(52) U.S. Cl.
USPC ........... 426/537; 426/534; 426/535; 426/536; 514/1.1; 514/79
(58) Field of Classification Search
USPC ................. 426/534, 535, 536, 537, 538, 650; 514/1.1, 79, 91, 95
See application file for complete search history.

(56) References Cited

U.S. PATENT DOCUMENTS

| | | | |
|---|---|---|---|
| 8,106,020 B2 | 1/2012 | Ohsu et al. | |
| 8,173,605 B2 | 5/2012 | Ohsu et al. | |
| 2009/0246835 A1 | 10/2009 | Iwatani et al. | |
| 2010/0105864 A1 | 4/2010 | Yoneda et al. | |
| 2010/0120698 A1 | 5/2010 | Nagasaki et al. | |
| 2010/0136197 A1 | 6/2010 | Eto et al. | |
| 2010/0183792 A1 | 7/2010 | Nagasaki et al. | |
| 2011/0046046 A1 | 2/2011 | Hara et al. | |
| 2011/0070270 A1 | 3/2011 | Kodera et al. | |
| 2011/0097805 A1 | 4/2011 | Ohsu et al. | |
| 2012/0034364 A1 | 2/2012 | Futaki et al. | |

FOREIGN PATENT DOCUMENTS

| | | |
|---|---|---|
| JP | 2009-514791 | 4/2009 |
| WO | WO2007/055393 | 5/2007 |
| WO | WO2011/081184 | 7/2011 |

OTHER PUBLICATIONS

Dugave, C., et al., "Synthesis of natural and non natural orthogonally protected lanthionines from N-tritylserine and allo-threonine derivatives," Tetrahedron: Asymmetry 1997;8(9):1453-1465.
Mustapa, M. F. M., et al., "Synthesis of cyclic peptides containing nor-lanthionine bridges via a triply-orthogonal protecting group strategy," Tetrahedron Lett. 2002;43:8363-8366.
Nakajima, K., et al., "Studies on 2-Aziridinecarboxylic Acid. IX. Convenient Synthesis of Optically Active S-Alkylcysteine, threo-S-Alkyl-β-methylcysteine, and Lanthionine Derivatives via the Ring-opening Reaction of Aziridine by Several Thiols," Bull. Chem. Soc. Jpn. 1983;56:520-522.
Ohsu, T., et al., "Involvement of the Calcium-sensing Receptor in Human Taste Perception," J. Biol. Chem. 2010;285(2):1016-1022.
International Search Report for PCT Patent App. No. PCT/JP2010/073720 (Mar. 8, 2011).
Written Opinion for PCT Patent App. No. PCT/JP2010/073720 (Mar. 8, 2011).

*Primary Examiner* — Leslie Wong
(74) *Attorney, Agent, or Firm* — Shelly Guest Cermak; Cermak Nakajima LLP

(57) ABSTRACT

The present invention provides a variety of compounds having a CaSR agonist activity which possesses a superior kokumi-imparting function, and more particularly provides a kokumi-imparting composition, which contains the foregoing compound, and/or another substance having a CaSR agonist activity, in combination. The present invention also provides a kokumi-imparting composition which includes a lanthionine derivative and/or another substance having a CaSR agonist activity.

11 Claims, No Drawings

SEQUENCE LISTING

<160> NUMBER OF SEQ ID NOS: 4

<210> SEQ ID NO 1
<211> LENGTH: 4924
<212> TYPE: DNA
<213> ORGANISM: Homo sapiens
<220> FEATURE:
<221> NAME/KEY: CDS
<222> LOCATION: (373)..(3609)
<223> OTHER INFORMATION:

<400> SEQUENCE: 1

| | |
|---|---|
| caacaggcac ctggctgcag ccaggaagga ccgcacgccc tttcgcgcag gagagtggaa | 60 |
| ggagggagct gtttgccagc accgaggtct tgcggcacag gcaacgcttg acctgagtct | 120 |
| tgcagaatga aaggcatcac aggaggcctc tgcatgatgt ggcttccaaa gactcaagga | 180 |
| ccacccacat tacaagtctg gattgaggaa ggcagaaatg gagattcaaa caccacgtct | 240 |
| tctattattt tattaatcaa tctgtagaca tgtgtcccca ctgcagggag tgaactgctc | 300 |
| caagggagaa acttctggga gcctccaaac tcctagctgt ctcatccctt gccctgagaa | 360 |
| gacggcagaa cc atg gca ttt tat agc tgc tgc tgg gtc ctc ttg gca ctc | 411 |
|             Met Ala Phe Tyr Ser Cys Cys Trp Val Leu Leu Ala Leu | |
|              1          5              10 | |
| acc tgg cac acc tct gcc tac ggg cca gac cag cga gcc caa aag aag | 459 |
| Thr Trp His Thr Ser Ala Tyr Gly Pro Asp Gln Arg Ala Gln Lys Lys | |
|  15              20               25 | |
| ggg gac att atc ctt ggg ggg ctc ttt cct att cat ttt gga gta gca | 507 |
| Gly Asp Ile Ile Leu Gly Gly Leu Phe Pro Ile His Phe Gly Val Ala | |
| 30            35              40             45 | |
| gct aaa gat caa gat ctc aaa tca agg ccg gag tct gtg gaa tgt atc | 555 |
| Ala Lys Asp Gln Asp Leu Lys Ser Arg Pro Glu Ser Val Glu Cys Ile | |
|             50              55             60 | |
| agg tat aat ttc cgt ggg ttt cgc tgg tta cag gct atg ata ttt gcc | 603 |
| Arg Tyr Asn Phe Arg Gly Phe Arg Trp Leu Gln Ala Met Ile Phe Ala | |
|  65              70              75 | |
| ata gag gag ata aac agc agc cca gcc ctt ctt ccc aac ttg acg ctg | 651 |
| Ile Glu Glu Ile Asn Ser Ser Pro Ala Leu Leu Pro Asn Leu Thr Leu | |
|         80              85              90 | |
| gga tac agg ata ttt gac act tgc aac acc gtt tct aag gcc ttg gaa | 699 |
| Gly Tyr Arg Ile Phe Asp Thr Cys Asn Thr Val Ser Lys Ala Leu Glu | |
|      95            100           105 | |
| gcc acc ctg agt ttt gtt gct caa aac aaa att gat tct ttg aac ctt | 747 |
| Ala Thr Leu Ser Phe Val Ala Gln Asn Lys Ile Asp Ser Leu Asn Leu | |
| 110             115            120           125 | |
| gat gag ttc tgc aac tgc tca gag cac att ccc tct acg att gct gtg | 795 |
| Asp Glu Phe Cys Asn Cys Ser Glu His Ile Pro Ser Thr Ile Ala Val | |
|              130            135           140 | |
| gtg gga gca act ggc tca ggc gtc tcc acg gca gtg gca aat ctg ctg | 843 |
| Val Gly Ala Thr Gly Ser Gly Val Ser Thr Ala Val Ala Asn Leu Leu | |
|                145            150           155 | |
| ggg ctc ttc tac att ccc cag gtc agt tat gcc tcc tcc agc aga ctc | 891 |
| Gly Leu Phe Tyr Ile Pro Gln Val Ser Tyr Ala Ser Ser Ser Arg Leu | |
|          160            165            170 | |
| ctc agc aac aag aat caa ttc aag tct ttc ctc cga acc atc ccc aat | 939 |
| Leu Ser Asn Lys Asn Gln Phe Lys Ser Phe Leu Arg Thr Ile Pro Asn | |
|         175            180           185 | |
| gat gag cac cag gcc act gcc atg gca gac atc atc gag tat ttc cgc | 987 |
| Asp Glu His Gln Ala Thr Ala Met Ala Asp Ile Ile Glu Tyr Phe Arg | |
| 190             195            200           205 | |

```
tgg aac tgg gtg ggc aca att gca gct gat gac gac tat ggg cgg ccg    1035
Trp Asn Trp Val Gly Thr Ile Ala Ala Asp Asp Asp Tyr Gly Arg Pro
            210                 215                 220 ggg att gag aaa ttc cga gag gaa gct gag gaa agg gat atc tgc atc    1083
Gly Ile Glu Lys Phe Arg Glu Glu Ala Glu Glu Arg Asp Ile Cys Ile
        225                 230                 235 gac ttc agt gaa ctc atc tcc cag tac tct gat gag gaa gag atc cag    1131
Asp Phe Ser Glu Leu Ile Ser Gln Tyr Ser Asp Glu Glu Glu Ile Gln
    240                 245                 250 cat gtg gta gag gtg att caa aat tcc acg gcc aaa gtc atc gtg gtt    1179
His Val Val Glu Val Ile Gln Asn Ser Thr Ala Lys Val Ile Val Val
    255                 260                 265 ttc tcc agt ggc cca gat ctt gag ccc ctc atc aag gag att gtc cgg    1227
Phe Ser Ser Gly Pro Asp Leu Glu Pro Leu Ile Lys Glu Ile Val Arg
270                 275                 280                 285 cgc aat atc acg ggc aag atc tgg ctg gcc agc gag gcc tgg gcc agc    1275
Arg Asn Ile Thr Gly Lys Ile Trp Leu Ala Ser Glu Ala Trp Ala Ser
            290                 295                 300 tcc tcc ctg atc gcc atg cct cag tac ttc cac gtg gtt ggc ggc acc    1323
Ser Ser Leu Ile Ala Met Pro Gln Tyr Phe His Val Val Gly Gly Thr
        305                 310                 315 att gga ttc gct ctg aag gct ggg cag atc cca ggc ttc cgg gaa ttc    1371
Ile Gly Phe Ala Leu Lys Ala Gly Gln Ile Pro Gly Phe Arg Glu Phe
    320                 325                 330 ctg aag aag gtc cat ccc agg aag tct gtc cac aat ggt ttt gcc aag    1419
Leu Lys Lys Val His Pro Arg Lys Ser Val His Asn Gly Phe Ala Lys
    335                 340                 345 gag ttt tgg gaa gaa aca ttt aac tgc cac ctc caa gaa ggt gca aaa    1467
Glu Phe Trp Glu Glu Thr Phe Asn Cys His Leu Gln Glu Gly Ala Lys
350                 355                 360                 365 gga cct tta cct gtg gac acc ttt ctg aga ggt cac gaa gaa agt ggc    1515
Gly Pro Leu Pro Val Asp Thr Phe Leu Arg Gly His Glu Glu Ser Gly
            370                 375                 380 gac agg ttt agc aac agc tcg aca gcc ttc cga ccc ctc tgt aca ggg    1563
Asp Arg Phe Ser Asn Ser Ser Thr Ala Phe Arg Pro Leu Cys Thr Gly
        385                 390                 395 gat gag aac atc agc agt gtc gag acc cct tac ata gat tac acg cat    1611
Asp Glu Asn Ile Ser Ser Val Glu Thr Pro Tyr Ile Asp Tyr Thr His
    400                 405                 410 tta cgg ata tcc tac aat gtg tac tta gca gtc tac tcc att gcc cac    1659
Leu Arg Ile Ser Tyr Asn Val Tyr Leu Ala Val Tyr Ser Ile Ala His
    415                 420                 425 gcc ttg caa gat ata tat acc tgc tta cct ggg aga ggg ctc ttc acc    1707
Ala Leu Gln Asp Ile Tyr Thr Cys Leu Pro Gly Arg Gly Leu Phe Thr
430                 435                 440                 445 aat ggc tcc tgt gca gac atc aag aaa gtt gag gcg tgg cag gtc ctg    1755
Asn Gly Ser Cys Ala Asp Ile Lys Lys Val Glu Ala Trp Gln Val Leu
            450                 455                 460 aag cac cta cgg cat cta aac ttt aca aac aat atg ggg gag cag gtg    1803
Lys His Leu Arg His Leu Asn Phe Thr Asn Asn Met Gly Glu Gln Val
        465                 470                 475 acc ttt gat gag tgt ggt gac ctg gtg ggg aac tat tcc atc atc aac    1851
Thr Phe Asp Glu Cys Gly Asp Leu Val Gly Asn Tyr Ser Ile Ile Asn
    480                 485                 490 tgg cac ctc tcc cca gag gat ggc tcc atc gtg ttt aag gaa gtc ggg    1899
Trp His Leu Ser Pro Glu Asp Gly Ser Ile Val Phe Lys Glu Val Gly
    495                 500                 505 tat tac aac gtc tat gcc aag aag gga gaa aga ctc ttc atc aac gag    1947
Tyr Tyr Asn Val Tyr Ala Lys Lys Gly Glu Arg Leu Phe Ile Asn Glu
510                 515                 520                 525
```

```
gag aaa atc ctg tgg agt ggg ttc tcc agg gag gtg ccc ttc tcc aac      1995
Glu Lys Ile Leu Trp Ser Gly Phe Ser Arg Glu Val Pro Phe Ser Asn
            530                 535                 540 tgc agc cga gac tgc ctg gca ggg acc agg aaa ggg atc att gag ggg      2043
Cys Ser Arg Asp Cys Leu Ala Gly Thr Arg Lys Gly Ile Ile Glu Gly
    545                 550                 555 gag ccc acc tgc tgc ttt gag tgt gtg gag tgt cct gat ggg gag tat      2091
Glu Pro Thr Cys Cys Phe Glu Cys Val Glu Cys Pro Asp Gly Glu Tyr
        560                 565                 570 agt gat gag aca gat gcc agt gcc tgt aac aag tgc cca gat gac ttc      2139
Ser Asp Glu Thr Asp Ala Ser Ala Cys Asn Lys Cys Pro Asp Asp Phe
575                 580                 585 tgg tcc aat gag aac cac acc tcc tgc att gcc aag gag atc gag ttt      2187
Trp Ser Asn Glu Asn His Thr Ser Cys Ile Ala Lys Glu Ile Glu Phe
590                 595                 600                 605 ctg tcg tgg acg gag ccc ttt ggg atc gca ctc acc ctc ttt gcc gtg      2235
Leu Ser Trp Thr Glu Pro Phe Gly Ile Ala Leu Thr Leu Phe Ala Val
            610                 615                 620 ctg ggc att ttc ctg aca gcc ttt gtg ctg ggt gtg ttt atc aag ttc      2283
Leu Gly Ile Phe Leu Thr Ala Phe Val Leu Gly Val Phe Ile Lys Phe
        625                 630                 635 cgc aac aca ccc att gtc aag gcc acc aac cga gag ctc tcc tac ctc      2331
Arg Asn Thr Pro Ile Val Lys Ala Thr Asn Arg Glu Leu Ser Tyr Leu
    640                 645                 650 ctc ctc ttc tcc ctg ctc tgc tgc ttc tcc agc tcc ctg ttc ttc atc      2379
Leu Leu Phe Ser Leu Leu Cys Cys Phe Ser Ser Ser Leu Phe Phe Ile
655                 660                 665 ggg gag ccc cag gac tgg acg tgc cgc ctg cgc cag ccg gcc ttt ggc      2427
Gly Glu Pro Gln Asp Trp Thr Cys Arg Leu Arg Gln Pro Ala Phe Gly
670                 675                 680                 685 atc agc ttc gtg ctc tgc atc tca tgc atc ctg gtg aaa acc aac cgt      2475
Ile Ser Phe Val Leu Cys Ile Ser Cys Ile Leu Val Lys Thr Asn Arg
            690                 695                 700 gtc ctc ctg gtg ttt gag gcc aag atc ccc acc agc ttc cac cgc aag      2523
Val Leu Leu Val Phe Glu Ala Lys Ile Pro Thr Ser Phe His Arg Lys
        705                 710                 715 tgg tgg ggg ctc aac ctg cag ttc ctg ctg gtt ttc ctc tgc acc ttc      2571
Trp Trp Gly Leu Asn Leu Gln Phe Leu Leu Val Phe Leu Cys Thr Phe
    720                 725                 730 atg cag att gtc atc tgt gtg atc tgg ctc tac acc gcg ccc ccc tca      2619
Met Gln Ile Val Ile Cys Val Ile Trp Leu Tyr Thr Ala Pro Pro Ser
735                 740                 745 agc tac cgc aac cag gag ctg gag gat gag atc atc ttc atc acg tgc      2667
Ser Tyr Arg Asn Gln Glu Leu Glu Asp Glu Ile Ile Phe Ile Thr Cys
750                 755                 760                 765 cac gag ggc tcc ctc atg gcc ctg ggc ttc ctg atc ggc tac acc tgc      2715
His Glu Gly Ser Leu Met Ala Leu Gly Phe Leu Ile Gly Tyr Thr Cys
            770                 775                 780 ctg ctg gct gcc atc tgc ttc ttc ttt gcc ttc aag tcc cgg aag ctg      2763
Leu Leu Ala Ala Ile Cys Phe Phe Phe Ala Phe Lys Ser Arg Lys Leu
        785                 790                 795 ccg gag aac ttc aat gaa gcc aag ttc atc acc ttc agc atg ctc atc      2811
Pro Glu Asn Phe Asn Glu Ala Lys Phe Ile Thr Phe Ser Met Leu Ile
    800                 805                 810 ttc ttc atc gtg tgg atc tcc ttc att cca gcc tat gcc agc acc tat      2859
Phe Phe Ile Val Trp Ile Ser Phe Ile Pro Ala Tyr Ala Ser Thr Tyr
815                 820                 825 ggc aag ttt gtc tct gcc gta gag gtg att gcc atc ctg gca gcc agc      2907
Gly Lys Phe Val Ser Ala Val Glu Val Ile Ala Ile Leu Ala Ala Ser
830                 835                 840                 845
```

```
ttt ggc ttg ctg gcg tgc atc ttc ttc aac aag atc tac atc att ctc      2955
Phe Gly Leu Leu Ala Cys Ile Phe Phe Asn Lys Ile Tyr Ile Ile Leu
            850                 855                 860 ttc aag cca tcc cgc aac acc atc gag gag gtg cgt tgc agc acc gca      3003
Phe Lys Pro Ser Arg Asn Thr Ile Glu Glu Val Arg Cys Ser Thr Ala
            865                 870                 875 gct cac gct ttc aag gtg gct gcc cgg gcc acg ctg cgc cgc agc aac      3051
Ala His Ala Phe Lys Val Ala Ala Arg Ala Thr Leu Arg Arg Ser Asn
            880                 885                 890 gtc tcc cgc aag cgg tcc agc agc ctt gga ggc tcc acg gga tcc acc      3099
Val Ser Arg Lys Arg Ser Ser Ser Leu Gly Gly Ser Thr Gly Ser Thr
            895                 900                 905 ccc tcc tcc tcc atc agc agc aag agc aac agc gaa gac cca ttc cca      3147
Pro Ser Ser Ser Ile Ser Ser Lys Ser Asn Ser Glu Asp Pro Phe Pro
910                 915                 920                 925 cag ccc gag agg cag aag cag cag cag ccg ctg gcc cta acc cag caa      3195
Gln Pro Glu Arg Gln Lys Gln Gln Gln Pro Leu Ala Leu Thr Gln Gln
                930                 935                 940 gag cag cag cag cag ccc ctg acc ctc cca cag cag caa cga tct cag      3243
Glu Gln Gln Gln Gln Pro Leu Thr Leu Pro Gln Gln Gln Arg Ser Gln
            945                 950                 955 cag cag ccc aga tgc aag cag aag gtc atc ttt ggc agc ggc acg gtc      3291
Gln Gln Pro Arg Cys Lys Gln Lys Val Ile Phe Gly Ser Gly Thr Val
            960                 965                 970 acc ttc tca ctg agc ttt gat gag cct cag aag aac gcc atg gcc cac      3339
Thr Phe Ser Leu Ser Phe Asp Glu Pro Gln Lys Asn Ala Met Ala His
            975                 980                 985 agg aat tct acg cac cag aac tcc ctg gag gcc cag aaa agc agc gat      3387
Arg Asn Ser Thr His Gln Asn Ser Leu Glu Ala Gln Lys Ser Ser Asp
990                 995                 1000                1005 acg ctg acc cga cac cag cca tta ctc ccg ctg cag tgc ggg gaa          3432
Thr Leu Thr Arg His Gln Pro Leu Leu Pro Leu Gln Cys Gly Glu
            1010                1015                1020 acg gac tta gat ctg acc gtc cag gaa aca ggt ctg caa gga cct          3477
Thr Asp Leu Asp Leu Thr Val Gln Glu Thr Gly Leu Gln Gly Pro
            1025                1030                1035 gtg ggt gga gac cag cgg cca gag gtg gag gac cct gaa gag ttg          3522
Val Gly Gly Asp Gln Arg Pro Glu Val Glu Asp Pro Glu Glu Leu
            1040                1045                1050 tcc cca gca ctt gta gtg tcc agt tca cag agc ttt gtc atc agt          3567
Ser Pro Ala Leu Val Val Ser Ser Ser Gln Ser Phe Val Ile Ser
            1055                1060                1065 ggt gga ggc agc act gtt aca gaa aac gta gtg aat tca taa              3609
Gly Gly Gly Ser Thr Val Thr Glu Asn Val Val Asn Ser
            1070                1075 aatgaagga gaagactggg ctagggagaa tgcagagagg tttcttgggg tcccagggaa     3669
gaggaatcgc cccagactcc tttcctctga ggaagaaggg ataatagaca catcaaatgc    3729
cccgaattta gtcacaccat cttaaatgac agtgaattga cccatgttcc ctttaaaatt    3789
aaaaaaaaga agagccttgt gtttctgtgg ttgcatttgt caaagcattg agatctccac    3849
ggtcagattt gctgttcacc cacatctaat gtctcttcct ctgttctatc ccacccaaca    3909
gctcagagat gaaactatgg ctttaaacta ccctccagag tgtgcagact gatgggacat    3969
caaatttgcc accactagag ctgagagtct gaaagacaga atgtcaccag tcctgcccaa    4029
tgccttgaca acagactgaa ttttaaatgt tcacaacata aggagaatgt atctcctcct    4089
atttatgaaa accatatgat attttgtctc ctacctgctg ctgctattat gtaacatcca    4149
gaaggtttgc acccctccta taccatatgt ctgcttctgt ccaggacatg atactgatgc    4209
```

-continued

```
catgtttaga ttccaggatc acaagaatca cctcaaattg ttaggaaggg actgcataaa    4269
ccaatgagct gtatctgtaa ttaatattcc tatatgtagc tttatcctta ggaaaatgct    4329
tctgttgtaa tagtccatgg acaatataaa ctgaaaatg tcagtctggt ttatataagg    4389
cagtattatt gagctctatt tccccacccc actatcctca ctcccataag ctaagcctta    4449
tgtgagcccc ttcagggact caagggtcca gaagtccctc ccatctctac cccaaagaat    4509
tcctgaagcc agatccaccc tatccctgta cagagtaagt tctcaattat tggcctgcta    4569
atagctgcta gggtaggaaa gcgtggttcc aagaaagatc caccctcaaa tgtcagagct    4629
atgttccctc cagcagtggt attaatactg ccggtcaccc aggctctgga gccagagaga    4689
cagaccgggg ttcaagccat ggcttcgtca tttgcaagct gagtgactgt aggcagggaa    4749
ccttaacctc tctaagccac agcttcttca tctttaaaat aaggataata atcattcttt    4809
cccctcagag ctcttatgtg gattaaacga gataatgtat ataaagtact ttagcctggt    4869
acctagcaca caataagcat tcaataaata ttagttaata ttattaaaaa aaaaa    4924
```

<210> SEQ ID NO 2
<211> LENGTH: 1078
<212> TYPE: PRT
<213> ORGANISM: Homo sapiens

<400> SEQUENCE: 2

```
Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Glu Ile Gln His Val Val
                245                 250                 255
```

-continued

```
Glu Val Ile Gln Asn Ser Thr Ala Lys Val Ile Val Phe Ser Ser
            260                 265                 270

Gly Pro Asp Leu Glu Pro Leu Ile Lys Glu Ile Val Arg Asn Ile
            275                 280                 285

Thr Gly Lys Ile Trp Leu Ala Ser Glu Ala Trp Ala Ser Ser Ser Leu
            290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                    325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
            355                 360                 365

Pro Val Asp Thr Phe Leu Arg Gly His Glu Glu Ser Gly Asp Arg Phe
            370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                    405                 410                 415

Ser Tyr Asn Val Tyr Leu Ala Val Tyr Ser Ile Ala His Ala Leu Gln
            420                 425                 430

Asp Ile Tyr Thr Cys Leu Pro Gly Arg Gly Leu Phe Thr Asn Gly Ser
            435                 440                 445

Cys Ala Asp Ile Lys Lys Val Glu Ala Trp Gln Val Leu Lys His Leu
450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                    485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
            515                 520                 525

Leu Trp Ser Gly Phe Ser Arg Glu Val Pro Phe Ser Asn Cys Ser Arg
530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                    565                 570                 575

Thr Asp Ala Ser Ala Cys Asn Lys Cys Pro Asp Asp Phe Trp Ser Asn
            580                 585                 590

Glu Asn His Thr Ser Cys Ile Ala Lys Glu Ile Glu Phe Leu Ser Trp
            595                 600                 605

Thr Glu Pro Phe Gly Ile Ala Leu Thr Leu Phe Ala Val Leu Gly Ile
            610                 615                 620

Phe Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe
                    645                 650                 655

Ser Leu Leu Cys Cys Phe Ser Ser Ser Leu Phe Phe Ile Gly Glu Pro
            660                 665                 670

Gln Asp Trp Thr Cys Arg Leu Arg Gln Pro Ala Phe Gly Ile Ser Phe
            675                 680                 685
```

```
Val Leu Cys Ile Ser Cys Ile Leu Val Lys Thr Asn Arg Val Leu Leu
    690             695                 700
Val Phe Glu Ala Lys Ile Pro Thr Ser Phe His Arg Lys Trp Trp Gly
705             710                 715                 720
Leu Asn Leu Gln Phe Leu Leu Val Phe Leu Cys Thr Phe Met Gln Ile
                725                 730                 735
Val Ile Cys Val Ile Trp Leu Tyr Thr Ala Pro Pro Ser Ser Tyr Arg
            740                 745                 750
Asn Gln Glu Leu Glu Asp Glu Ile Ile Phe Ile Thr Cys His Glu Gly
        755                 760                 765
Ser Leu Met Ala Leu Gly Phe Leu Ile Gly Tyr Thr Cys Leu Leu Ala
    770                 775                 780
Ala Ile Cys Phe Phe Phe Ala Phe Lys Ser Arg Lys Leu Pro Glu Asn
785                 790                 795                 800
Phe Asn Glu Ala Lys Phe Ile Thr Phe Ser Met Leu Ile Phe Phe Ile
                805                 810                 815
Val Trp Ile Ser Phe Ile Pro Ala Tyr Ala Ser Thr Tyr Gly Lys Phe
            820                 825                 830
Val Ser Ala Val Glu Val Ile Ala Ile Leu Ala Ala Ser Phe Gly Leu
        835                 840                 845
Leu Ala Cys Ile Phe Phe Asn Lys Ile Tyr Ile Ile Leu Phe Lys Pro
    850                 855                 860
Ser Arg Asn Thr Ile Glu Glu Val Arg Cys Ser Thr Ala Ala His Ala
865                 870                 875                 880
Phe Lys Val Ala Ala Arg Ala Thr Leu Arg Arg Ser Asn Val Ser Arg
                885                 890                 895
Lys Arg Ser Ser Ser Leu Gly Gly Ser Thr Gly Ser Thr Pro Ser Ser
            900                 905                 910
Ser Ile Ser Ser Lys Ser Asn Ser Glu Asp Pro Phe Pro Gln Pro Glu
    915                 920                 925
Arg Gln Lys Gln Gln Gln Pro Leu Ala Leu Thr Gln Gln Glu Gln Gln
930                 935                 940
Gln Gln Pro Leu Thr Leu Pro Gln Gln Arg Ser Gln Gln Gln Pro
945                 950                 955                 960
Arg Cys Lys Gln Lys Val Ile Phe Gly Ser Gly Thr Val Thr Phe Ser
                965                 970                 975
Leu Ser Phe Asp Glu Pro Gln Lys Asn Ala Met Ala His Arg Asn Ser
            980                 985                 990
Thr His Gln Asn Ser Leu Glu Ala Gln Lys Ser Ser Asp Thr Leu Thr
        995                 1000                1005
Arg His Gln Pro Leu Leu Pro Leu Gln Cys Gly Glu Thr Asp Leu
    1010                1015                1020
Asp Leu Thr Val Gln Glu Thr Gly Leu Gln Gly Pro Val Gly Gly
    1025                1030                1035
Asp Gln Arg Pro Glu Val Glu Asp Pro Glu Glu Leu Ser Pro Ala
    1040                1045                1050
Leu Val Val Ser Ser Ser Gln Ser Phe Val Ile Ser Gly Gly Gly
    1055                1060                1065
Ser Thr Val Thr Glu Asn Val Val Asn Ser
    1070                1075

<210> SEQ ID NO 3
<211> LENGTH: 49
<212> TYPE: DNA
```

```
<213> ORGANISM: Artificial
<220> FEATURE:
<223> OTHER INFORMATION: primer

<400> SEQUENCE: 3
actaatacga ctcactatag ggaccatggc attttatagc tgctgctgg                49

<210> SEQ ID NO 4
<211> LENGTH: 29
<212> TYPE: DNA
<213> ORGANISM: Artificial
<220> FEATURE:
<223> OTHER INFORMATION: primer

<400> SEQUENCE: 4
ttatgaattc actacgtttt ctgtaacag                                      29
```

LANTHIONINE DERIVATIVES

This application is a Continuation of, and claims priority under 35 U.S.C. §120 to, International Application No. PCT/JP2010/073720, filed Dec. 28, 2010, and claims priority therethrough under 35 U.S.C. §119 to Japanese Patent Application No. 2009-298010, filed Dec. 28, 2009, the entireties of which are incorporated by reference herein. Also, the Sequence Listing filed electronically herewith is hereby incorporated by reference (File name: 2012-06-26T_US-484_Seq_List; File size: 27 KB; Date recorded: Jun. 26, 2012).

BACKGROUND OF THE INVENTION

1. Field of the Invention

The present invention relates to a novel compound having CaSR agonist activity, and a food composition containing the novel compound as well as a kokumi-imparting composition.

2. Brief Description of the Related Art

In recent years, consumers' demands on taste and palatability of foods has increased due to, for instance, the diversification of human eating habits, and this correspondingly results in an increase in the need for the development of an excellent kokumi-imparting agents and compositions, which can impart "kokumi" to various foods. In this respect, the kokumi cannot be expressed simply in terms of the five basic tastes, i.e., sweet, salty, sour, bitter, and the taste called "UMAMI", because the taste and palate are reinforced even in the marginal tastes, which relate to the foregoing five basic tastes, but include such characteristics such as the thickness, growth (mouthfullness), continuity, and harmony, in addition to the foregoing five basic tastes.

The "calcium sensing receptor" (CaSR) can also be referred to as the "calcium receptor", and the signals emitted from the calcium sensing receptor can control a variety of functions within a living body and the substances having such a CaSR agonist activity can thus be used and incorporated into foods or the like as a kokumi-imparting agent (see, Pamphlet of the Published International Patent No. 2007/055393 and The Journal of Biological Chemistry, 2010, 285 (2), pp. 1016-22).

In addition, glutathione has been known, for a long time, as a compound having a kokumi-imparting activity. However, glutathione contains cysteine, which includes a sulfur atom and therefore, glutathione suffers from a number of problems that must be overcome and include for instance, a lack of stability and the emission of a sour smell.

Accordingly, compounds having a CaSR agonist activity have been sought after and researched, so to find a substance which has a more excellent kokumi-imparting function, in particular, an initial taste type kokumi-imparting function, which is also highly stability and can easily be produced at a low cost. Such compounds, can compositions containing one or more of these compounds are desired to impart kokumi to various foods.

SUMMARY OF THE INVENTION

It is a principal aspect of the present invention to search for a variety of compounds having a CaSR agonist activity in order to obtain a substance having a more excellent kokumi-imparting function, and more particularly to provide a kokumi-imparting agent or composition, which contains the foregoing substance, and/or another substance having a CaSR agonist activity as well, in combination. It is a further aspect of the present invention to provide a food composition containing the substance in a predetermined concentration.

As a result, a group of novel lanthionine derivatives have been found which have a structure represented by the following general formula (I). These compounds have a high CaSR agonist activity and an extremely excellent kokumi-imparting function. Furthermore, the addition of such a compound permits the production of a favorable food composition whose kokumi (rich flavor) is strengthened or improved.

More specifically, it is an aspect of the present invention to provide a compound having a structure represented by the following general formula (I) or an edible salt thereof:

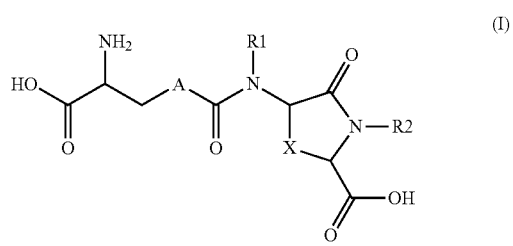

(I)

wherein R1 and R2 each independently represent a hydrogen atom or a lower alkyl group having 1 to 3 carbon atoms;

A represents a methylene group or an oxy group (—O—); and

X represents an alkylene group having 1 to 5 carbon atoms, provided that one of the methylene groups appearing in the alkylene group may be substituted with a thio group (—S—), a disulfide group (—S—S—), an oxy group (—O—), an imino group (—NH—) or an alkyl-imino group having 1 to 3 carbon atoms (—NRa—, wherein Ra represents an alkyl group having 1 to 3 carbon atoms) and that the alkylene group may further be substituted with 1 to 6 alkyl groups each having 1 to 3 carbon atoms.

Moreover, it is a further aspect of the present invention to provide a food composition comprising a compound represented by the foregoing formula (I) or an edible salt thereof in an amount ranging from 10 ppb to 99.9% by mass.

The present invention further provides a kokumi-imparting agent containing, as an effective component, a compound represented by the foregoing formula (I) or an edible salt thereof (hereunder this is also referred to as "the kokumi-imparting agent of the present invention").

In addition, the present invention likewise provides a composite kokumi-imparting agent, which comprises (a) a compound represented by the foregoing general formula (I) or an edible salt thereof; and (b) one or at least two amino acids or peptides selected from the group consisting of γ-Glu-X-Gly (wherein X represents an amino acid or an amino acid derivative), γ-Glu-Val-Y (wherein Y represents an amino acid or an amino acid derivative), γ-Glu-Abu, γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met (O), γ-Glu-γ-Glu-Val, γ-Glu-Val-NH$_2$, γ-Glu-Val-ol, γ-Glu-Ser, γ-Glu-Tau, γ-Glu-Cys (S-Me) (O), γ-Glu-Leu, γ-Glu-Ile, γ-Glu-t-Leu and γ-Glu-Cys (S-Me).

Moreover, the present invention also provides a compound having a structure represented by the following general formula (IA) or a chemically acceptable salt thereof, which is useful as an intermediate for the preparation of the compound represented by the foregoing general formula (I) or the edible salt thereof.

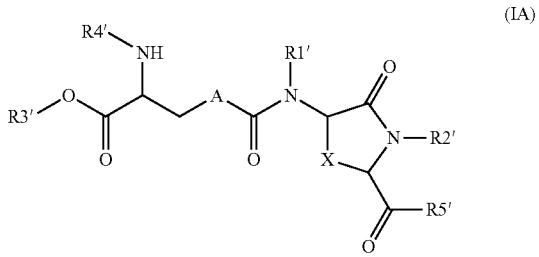

(IA)

wherein R1' and R2' each independently represent a hydrogen atom or an alkyl group having 1 to 3 carbon atoms;

R3' represents a hydrogen atom, an alkyl group having 1 to 4 carbon atoms, a benzyl group, or a 9-fluorenylmethyl group;

R4' represents a t-butoxycarbonyl group, a benzyloxy-carbonyl group, or a 9-fluorenylmethyl-oxycarbonyl group;

R5' represents a hydroxyl group, an alkoxy group having 1 to 4 carbon atoms, a benzyloxy group, an amino group ($—NH_2$) or an alkylamino group having 1 to 3 carbon atoms;

A represents a methylene group or an oxy group; and

X represents an alkylene group having 1 to 5 carbon atoms, provided that one of the methylene groups included in the alkylene group may be substituted with a thio group, a disulfide group, an oxy group, an imino group or an alkyl-imino group having 1 to 3 carbon atoms and that the alkylene group may further be substituted with 1 to 6 alkyl groups each having 1 to 3 carbon atoms.

The present invention can also provide a kokumi-imparting agent and a kokumi-imparting composition, which have an extremely excellent kokumi-imparting function and excellent stability and which can easily be prepared at a low cost. Moreover, the present invention can likewise provide an excellent food composition which contains a substance having an excellent kokumi-imparting function in a concentration equal to or higher than a predetermined level.

DESCRIPTION OF THE PREFERRED EMBODIMENTS

The term "alkyl group having 1 to 3 carbon atoms" means a linear or branched alkyl group and more specifically, the alkyl group having 1 to 3 carbon atoms can be, for instance, a methyl group, an ethyl group, an n-propyl group, and an isopropyl group, and particular examples include, for instance, a methyl group or an ethyl group.

Moreover, the term "alkyl-imino group having 1 to 3 carbon atoms" means an imino group substituted with an alkyl group having 1 to 3 carbon atoms such as those listed above.

Particular examples of the compounds represented by the foregoing general formula (I) include those specified below:

The compounds represented by the general formula (I), wherein R1 and R2 each can represent a hydrogen atom;

A preferably represents a methylene group;

X preferably represents a trimethylene group in which one of the methylene groups included therein is substituted with a thio group and, in particular, a group: $—CH_2—S—CH_2—$; or X preferably represents a tetramethylene group in which one of the methylene groups thereof is replaced with a thio group, or a trimethylene group which is substituted with an alkyl group having 1 to 3 carbon atoms and one of the methylene groups of which is replaced with a thio group, and X can be a group selected from $—CH_2—S—CH_2—CH_2—$, $—CH(CH_3)—S—CH_2—$, or $—CH_2—S—CH(CH_3)—$; or X can be a trimethylene group.

Regarding the carbon atoms a and b present in the ring structure appearing in the compound represented by the general formula (I), compounds having any possible steric configuration can be used, but a particular configuration thereof can include those represented by the following general formulas (I-1) and (I-2), with the configuration represented by the formula (I-1) being preferred particular example. In addition, with respect to the carbon c present in the compound, particular examples are the compounds each having an S-configuration:

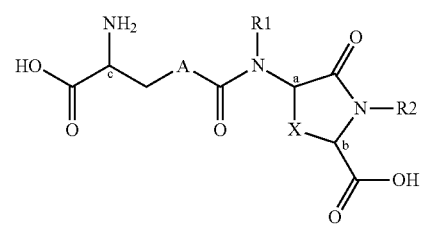

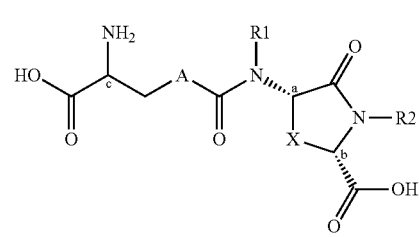

(I-1)

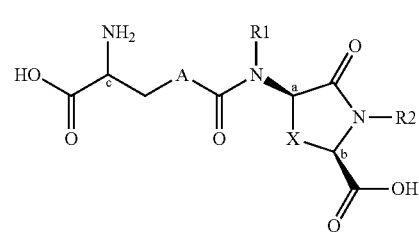

(I-2)

More specifically, the compounds specified below or edible salts thereof can be used as the compounds represented by the general formula (I) or the edible salts thereof:

The compounds represented by the general formula (I) in which R1 and R2 each represent a hydrogen atom; A represents a methylene group; and X represents a trimethylene group substituted with a thio group;

The compounds represented by the following general formula (I-1a):

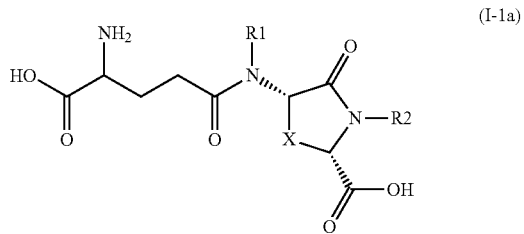

(I-1a)

The compounds represented by the following general formula (IIa):

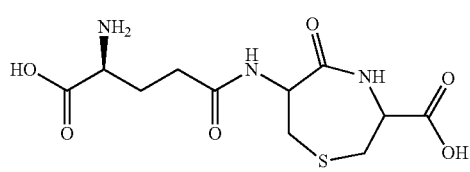
(IIa)

The compounds having the following steric configuration and represented by the foregoing general formula (IIa); among these compounds, either of the compounds represented by the following structural formulas 8a to 8d can be used, and a particular example is the compound of the structural formula 8b:

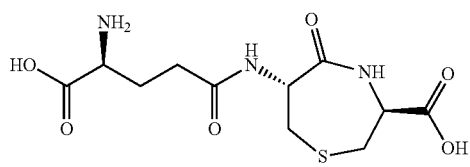
8a

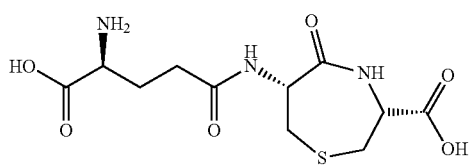
8b

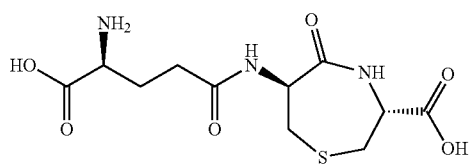
8c

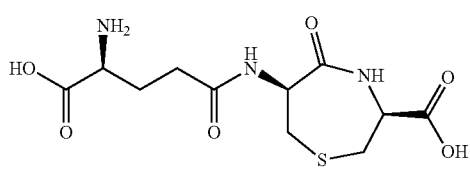
8d

The compounds represented by the foregoing general formula (I) in which R1 and R2 each represent a hydrogen atom; A represents a methylene group; X represents a tetramethylene group substituted with a thio group or a trimethylene group which is substituted with an alkyl group having 1 to 3 carbon atoms and in which one of the methylene groups thereof is replaced with a thio group;

The compounds represented by the following general formulas (IIb) and (IIc):

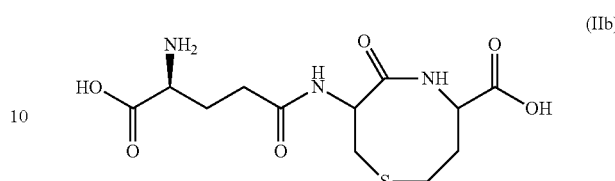
(IIb)

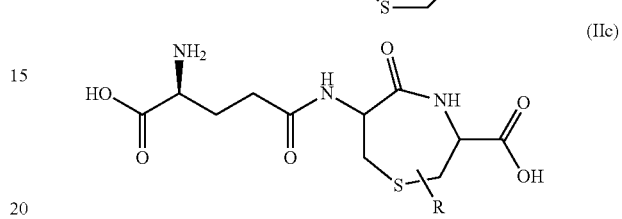
(IIc)

wherein R represents an alkyl group having 1 to 3 carbon atoms.

Specific examples of the foregoing edible salts include, for instance, ammonium salts, alkali metal salts (examples can include, for instance, sodium salts and potassium salts) and alkaline earth metal salts (examples can include, for instance, calcium salts and magnesium salts); and salts with organic bases such as lysine salts and alginates for the sufficiently acidic compounds. Furthermore, the edible salts can likewise include, for instance, inorganic salts with, for instance, hydrochloric acid; or salts with organic acids such as acetic acid, citric acid, lactic acid, succinic acid, fumaric acid and malic acid for the sufficiently basic compounds.

In addition, examples of the foregoing chemically acceptable salts include those listed above in connection with the edible salts.

Preparation Methods

Typical methods for the preparation of the compounds will be described below in detail:

In this connection, it is sometimes effective, from the viewpoint of the production technique, in the following preparation methods, that some functional groups included in raw materials or intermediates are replaced with appropriate protective groups, i.e., groups each capable of being easily converted into the initial functional groups, depending on the kinds of the functional groups. Thereafter, the protective groups can, if necessary, be removed to thus give each desired compound. As such functional groups, there may be listed, for instance, amino group, hydroxyl group, and carboxyl group and examples of protective groups therefor include, for instance, t-butoxycarbonyl group (Boc), benzyloxycarbonyl group (Cbz) and 9-fluorenylmethoxycarbonyl group (Fmoc) as protective groups for the amino group; and t-butyl group (t-Bu) and benzyl group (Bn or Bzl) as protective groups for the carboxyl group. These protective groups are described in more detail in the article entitled: "Protective Groups in Organic Synthesis", the third edition, Written by T. W. Green & P. G. M. Wuts, published by JOHN WILLY & SONS, INC. These protective groups may appropriately be selected and used while taking into consideration the specific reaction conditions. The method disclosed in the foregoing reference article can appropriately be applied to introduce a protective group and to remove the same (deblocking). For instance, this indicates that the functional groups Prot 1 and Prot 2 described in the following production method are used as such functional groups, but the present invention is not restricted to these specific examples.

The compound represented by the general formula (I) can, for instance, be prepared according to the synthesis scheme I detailed below:

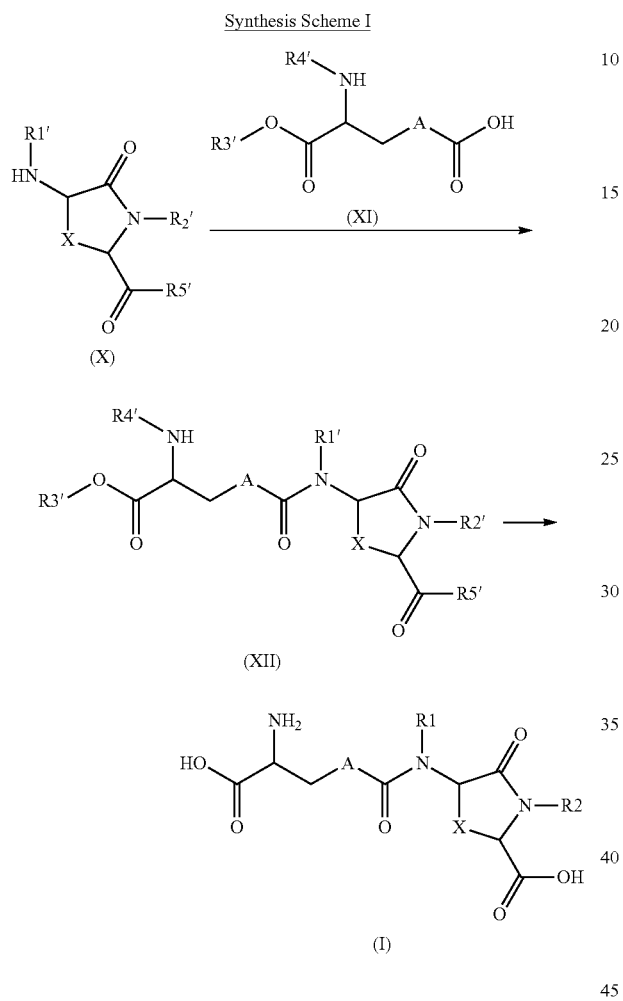

Wherein the definitions of the substituents appearing in these formulas are the same as those specified above in connection with the foregoing general formula (I) or (IA).

A compound (X) is condensed with a glutamic acid derivative (XI) in the presence of a base while using a condensation agent to thus form a γ-glutamyl compound (XII). Thereafter, all of the protective groups for the carboxyl and amino groups of the compound (XII) are removed to thus give a desired compound (I).

The compound represented by the general formula (I) prepared according to the foregoing method can be isolated and purified by any known technique such as concentration under reduced pressure, extraction with a solvent, crystallization, and/or chromatography.

In addition, the compound represented by the foregoing general formula in which R1' and R2' each represent a hydrogen atom and X is a group: —$CH_2$—S—$CH_2$— as an example of the starting material (X) can, for instance, be prepared according to the following synthesis scheme II given below:

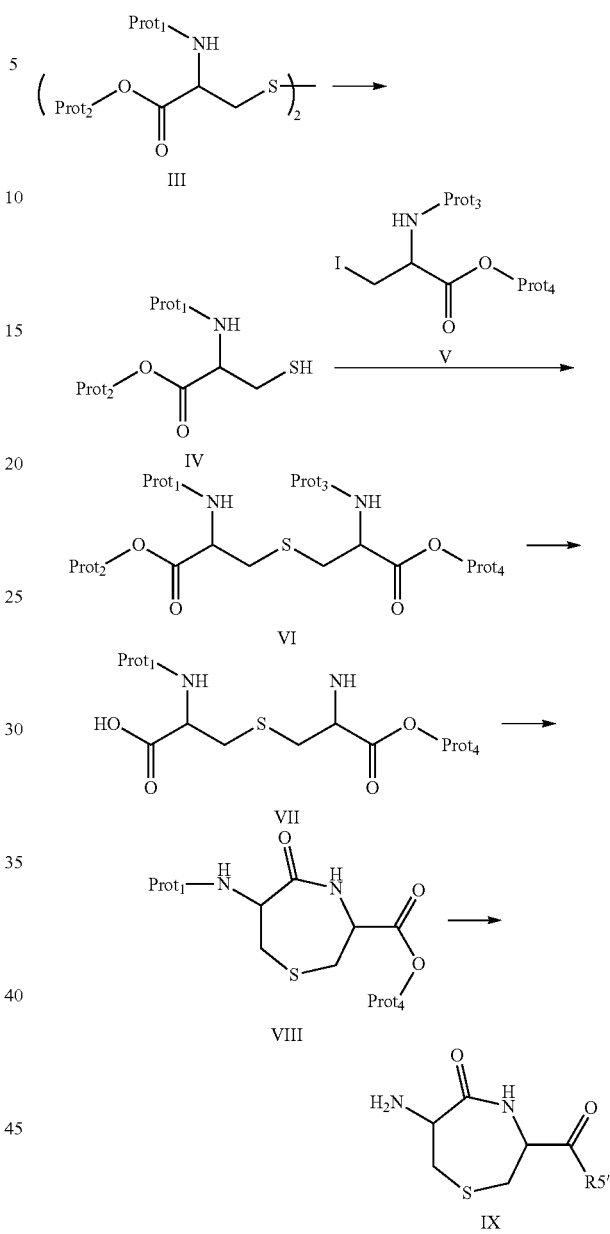

wherein Prot 1 to Prot 4 independently represent appropriate protective groups, respectively.

If explaining in detail, a compound (III) is first reduced with triphenylphosphine or the like to form a thiol (IV). Then a thioether compound (VI) is prepared through the reaction between the resulting compound (IV) and an alkyl halide in the presence of a base. After partially removing the protective groups of the resulting compound (VI), the latter is converted into a cyclic compound (VIII) in the presence of a base while using a condensation agent. After the removal of the protective group of the amino group present on the compound (VIII), then the resulting compound is condensed with a glutamic acid derivative (X) using an appropriate condensation agent.

The compound represented by the general formula (X) prepared according to the foregoing procedures can be isolated and purified by the use of any known technique such as concentration under reduced pressure, extraction with a solvent, crystallization, and/or chromatography.

The foregoing starting material (X) in which X represents a tetramethylene group substituted with a thio group can be synthesized according to, for instance, the following synthesis scheme III, and according to the same method used for the preparation of the foregoing compound:

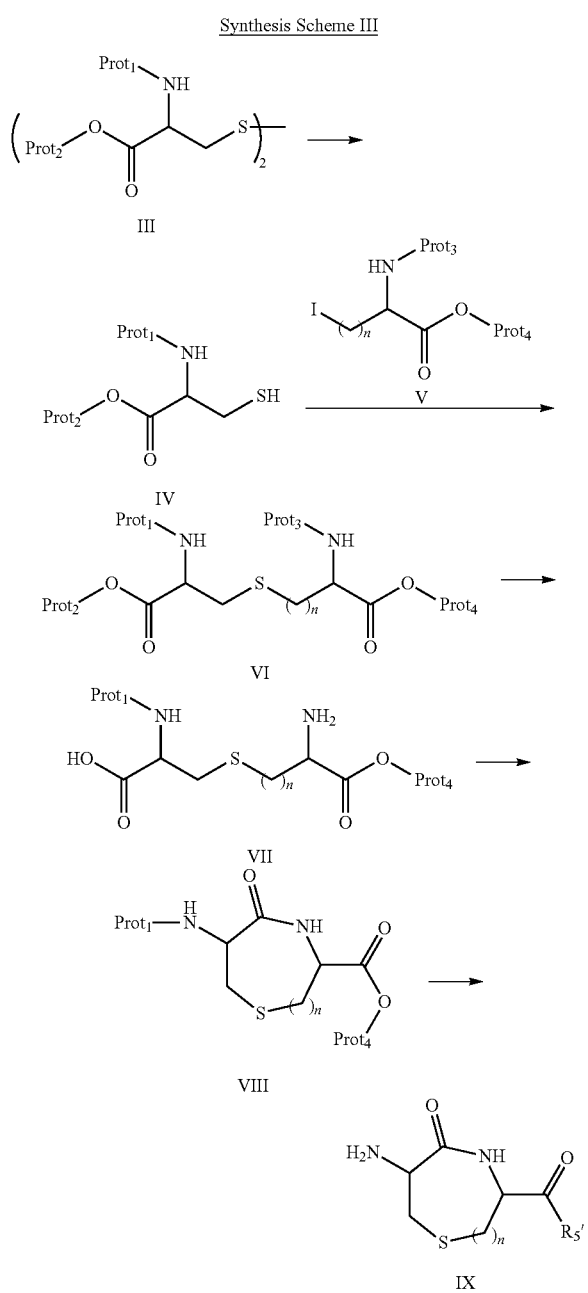

Wherein the definitions of the substituents appearing in these compounds are the same as those already specified above and n is 2.

The foregoing starting material (X) in which X represents a trimethylene group substituted with a thio group, which is substituted with an alkyl group having 1 to 3 carbon atoms, can be synthesized according to the following synthesis scheme IV, and according to the same procedures used above in connection with the preparation of the foregoing compound:

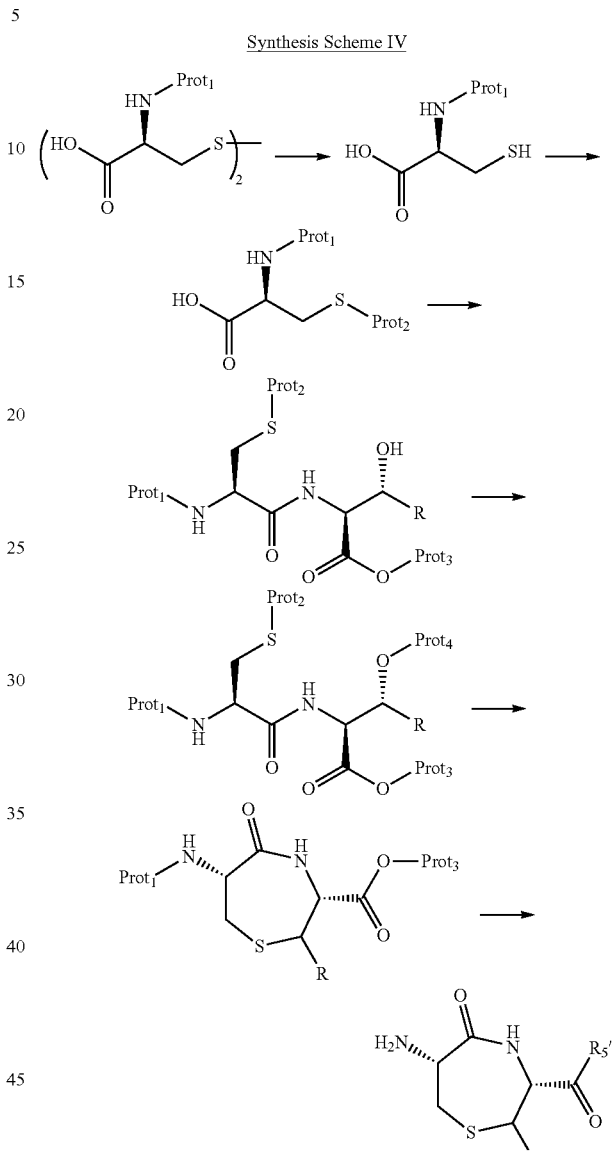

Wherein the definitions of the substituents appearing in these compounds are the same as those already specified above.

The foregoing starting material (X) in which X represents a trimethylene group substituted with an oxy group can be synthesized according to, for instance, the following synthesis scheme V:

Synthesis Scheme V

1) Method for the Synthesis of Cyclic Compounds using Aziridine Derivatives:

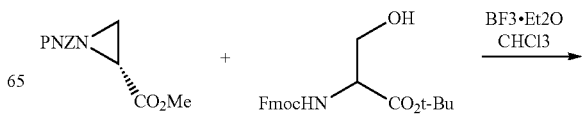

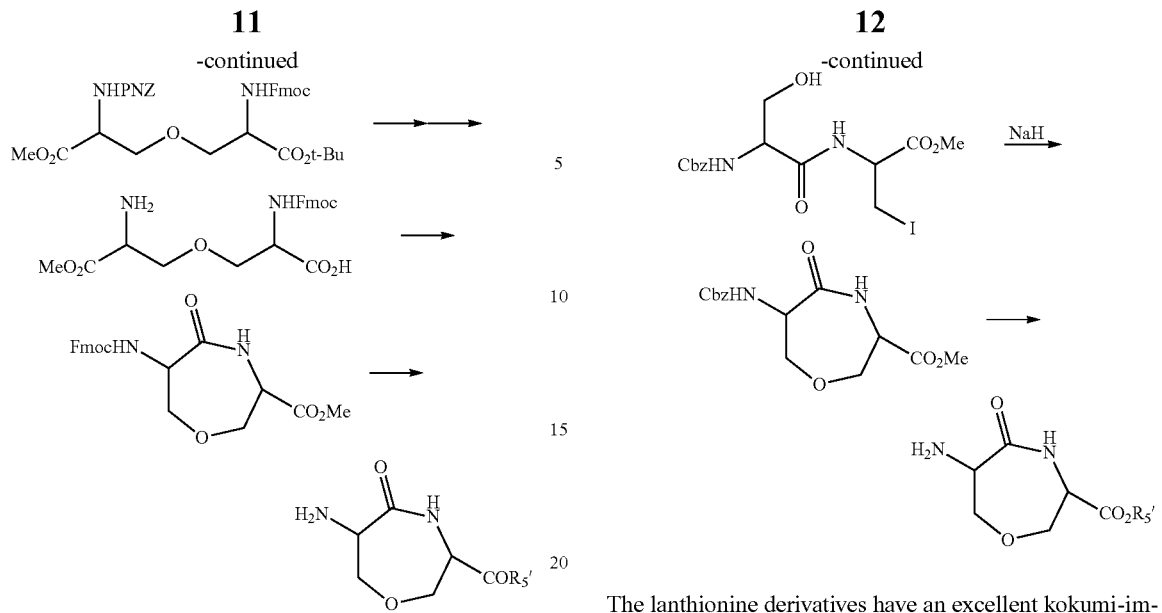

2) Method for the Synthesis of Cyclic Compounds through the Intermolecular Etherification:

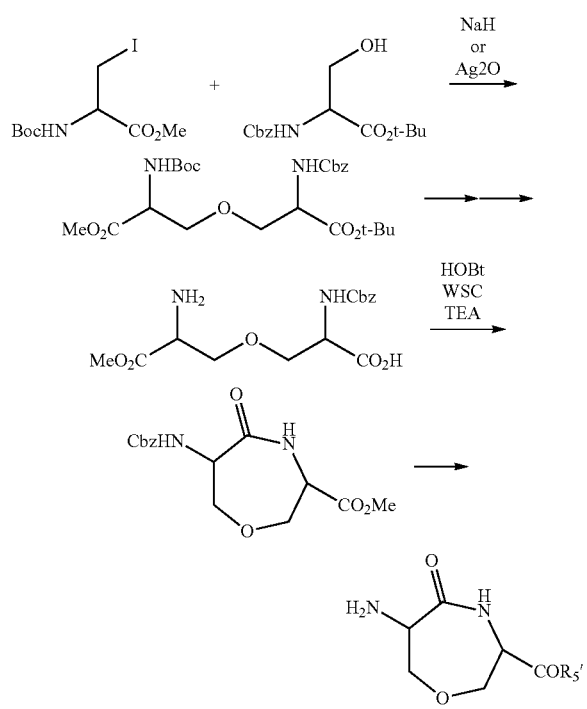

3) Method for the Synthesis of Cyclic Compounds through the Intramolecular Etherification:

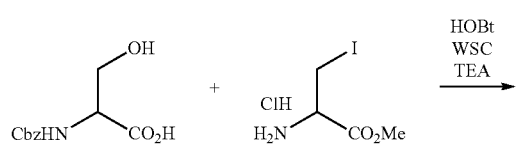

The lanthionine derivatives have an excellent kokumi-imparting effect on other substances and therefore, the derivative can be used as a kokumi-imparting agent or in a composition. The lanthionine derivatives can be used in such a manner that it is incorporated into a food composition in need of kokumi in an amount ranging from 10 ppb to 99.9% by mass, 0.05 ppm to 99.9% by mass, or 0.1 ppm to 99.9% by mass on the basis of the total mass of the food composition. More specifically, according to another aspect, the lanthionine derivatives can be used in a food composition in an amount ranging from 0.05 ppm to 99.9%.

Moreover, if using the lanthionine derivatives in combination with at least one other raw material for seasonings, such as amino acids such as sodium glutamate (MSG), nucleic acids such as inosine mono-phosphate (IMP), inorganic salts such as sodium chloride, organic acids such as citric acid, and various yeast extracts, the former can provide a seasoning which enhances kokumi as compared with that observed when using such other raw material for seasonings, by itself. The concentration of the lanthionine derivative when using the same in combination with the foregoing other raw material for seasoning can appropriately be set by one of ordinary skill in the art while taking into consideration the results of sensory or organoleptic evaluation. In an example, however, it would be sufficient that the lanthionine derivative is used in an amount ranging from about 0.1 ppm to about 500 ppm as expressed in terms of the final concentration.

The term "kokumi" can mean a taste which cannot be expressed by the five basic tastes, i.e., sweet, salty, sour, bitter, and umami (deliciousness), and more specifically the term can mean a marginal taste of the five basic tastes, such as thickness, growth (mouthfullness), continuity, and harmony, in which such marginal tastes are enhanced in addition to the five basic tastes. In this respect, the term "kokumi-imparting" can mean that not only the five basic tastes represented by sweet, salty, sour, bitter and UMAMI taste are enhanced, but also the marginal tastes with respect to the foregoing five basic tastes such as thickness, growth (mouthfullness), continuity, and harmony are imparted to any desired food. Alternatively, this may likewise be called a "flavor-enhancing effect". Accordingly, the compound can likewise be referred to as a "flavor enhancer". The compound can be used to enhance a sweet taste, a salty taste, a sour taste, a bitter taste, or an umami.

In addition, the taste and palatability can vary over time after placing the food in the mouth, but it can be referred to as initial taste, middle taste and after taste in the order of the time elapsed after eating. This is simply a relative concept. Generally speaking, however, the initial taste, the middle taste and the after taste are defined to be the flavor sensed at from 0 to 2 seconds, from 2 to 5 seconds and at or after 5 seconds, after eating, respectively. Moreover, the combined initial and middle tastes are comprehensively referred to as "initial-middle taste" and the combined middle and after tastes are comprehensively referred to as "middle-after taste". Furthermore, the "initial-middle taste" is defined to be the taste sensed from 0 to 5 seconds after eating, and the "middle-after taste" is defined to be the taste sensed from 2 seconds to around 30 seconds after eating. Regarding the evaluation based on the foregoing three divisions, it would be difficult for the panelists (persons who eat a sample and evaluate the taste thereof) to concentrate their attention on the evaluation of each specific sample and therefore, it is common to use the evaluation based on the two divisions.

The effect of a substance having a CaSR activity on the kokumi and flavoring pattern can be confirmed by a method such as an organoleptic test for evaluating the taste of a sample using panelists. As such an organoleptic test for evaluating the taste of a sample, there may be listed, for instance, the test disclosed in Examples of the instant patent specification, but the present invention is not restricted to these specific methods.

The term "CaSR" can mean the calcium sensing receptor, which belongs to class C of the 7-time transmembrane receptors, and it can also be referred to as calcium receptor. The term "CaSR agonist" can mean a substance which is bound to the CaSR to thereby activate the same. In addition, the term "activate CaSR" used in this specification means that a ligand is bound to CaSR to activate a guanine nucleotide-linked protein and to thereby transmit signals. Moreover, the term "CaSR agonist activity" can mean the properties of a substance such that it can be bound to the CaSR to thus activate the same.

A method for screening a compound having such a CaSR agonist activity, which includes the following steps, will specifically be described below, but the present invention is by no means limited to these steps at all.
1) A step of adding a test substance to a CaSR activity-determining system for the determination of the CaSR activity and of determining the CaSR activity of the test substance;
2) A step of comparing the CaSR activity observed when the test substance is added with that observed when the test substance is not added;
3) A step for selecting a specific test substance which shows a CaSR agonist activity when a test substance is added.

The CaSR activity can be determined by, for instance, using a system which makes use of a cell capable of expressing CaSR. The cell may be one capable of endogeneously expressing CaSR or a recombinant cell carrying a CaSR gene exogenously introduced into the same. The foregoing CaSR activity-determining system is not restricted to any particular one inasmuch as it can detect the bond or reaction between an activation substance and CaSR when adding an extracellular ligand (the activation substance) specific to CaSR; or it can transmit detectable signals within the cell in response to the formation of bond or reaction between the activation substance and CaSR. When a CaSR activity is detected through the reaction with a test substance, the test substance can be so judged that it has a CaSR-stimulation activity.

As the foregoing CaSR, a human CaSR encoded by the human CaSR gene registered under the GenBank Accession No. NM_000388 can be used. In this connection, the CaSR is not restricted to the protein coded by the gene having the foregoing gene sequence and may be proteins each coded by any gene having a homology with the foregoing sequence of not less than 60%, not less than 80% or not less than 90%, inasmuch as the gene can code a protein having a CaSR function. In the meantime, the CaSR function can be examined by expressing these genes within a cell and determining any change of the electric current observed when calcium is added or any change of the concentration in calcium ions within the cells.

The origin or source of the foregoing CaSR is not restricted, and specific examples thereof include not only CaSR derived from man, but also those derived from all kinds of animals including, for instance, mouse, rat, and dog.

As has been described above, the CaSR activity can be confirmed by the use of, for instance, living cells which can express CaSR or a fragment thereof, cell membranes which can express CaSR or a fragment thereof, or an in vitro system containing CaSR or a protein as a fragment thereof.

The following is an example of such a method for confirming the CaSR activity, which makes use of a living cell, but the present invention is not restricted to this method.

The expression of CaSR is carried out by cultivating cells such as the oocytes from xenopus, the ovary cells derived from hamster, or the human fetal renal cells. More specifically, the expression of CaSR can be realized by introducing into host cells, a product obtained by the transformation of a plasmid maintaining exogenous genes with cloned CaSR gene in the form of the recombinant plasmid per se, or the cRNA obtained by the use of the recombinant plasmid as a template. An electrophysiological method or a fluorescent indicator for detecting any increase in the calcium content of the cells can be used for the detection of a desired reaction.

Initially, the expression of CaSR is confirmed by the detection of the response to calcium or a specific activation agent. The oocytes which showed the generation of an intracellular electric current in response to a calcium concentration on the order of about 5 mM can be used; or the cultivated cells for which the emission of fluorescence due to a fluorescent indicator is observed. Then the same procedures used above are repeated while changing the calcium concentration to thus determine the calcium concentration-dependency. Subsequently, a solution of a test substance having a concentration ranging from about 1 µM to about 1 mM is prepared, the resulting solution is added to ovocytes or cultured cells and the CaSR activity in the presence of the foregoing test substance is measured to thus determine the CaSR agonist activity of the test substance.

Moreover, as tests for determining the CaSR activity, there may be listed, for instance, those described in the following Test Examples, but the present invention is not restricted to these specific ones.

In the kokumi-imparting composition according to the present invention, the amino acids or peptides used in combination with the lanthionine derivative can be one or at least two amino acids or peptides such as γ-Glu-X-Gly wherein X represents an amino acid or an amino acid derivative, γ-Glu-Val-Y wherein Y represents an amino acid or an amino acid derivative, γ-Glu-Abu, γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met (O), γ-Glu-γ-Glu-Val, γ-Glu-Val-NH$_2$, γ-Glu-Val-ol, γ-Glu-Ser, γ-Glu-Tau, γ-Glu-Cys (S-Me) (O), γ-Glu-Leu, γ-Glu-Ile, γ-Glu-t-Leu and γ-Glu-Cys (S-Me). In this respect, the term "amino acid" can include neutral amino acids such as Gly, Ala, Val, Leu, Ile, Ser, Thr, Cys, Met, Asn, Gln, Pro, Hyp and t-Leu; acidic amino acids such as Asp and Glu; basic amino acids such as Lys, Arg and His; aromatic amino acids such as Phe, Tyr and Trp; and homoserine, citrulline, ornithine, α-amino butyric acid, norvaline, norleucine, and taurine. Moreover, the amino acids or peptides used in combination with the lanthionine derivative may likewise be, for instance, artificially synthesized amino acids (each having a non-proteinaceous configuration) such as tert-leucine, cycloleucine, α-amino-isobutyric acid, L-penicillamine, allo-threonine and allo-isoleucine. In this connection, the symbol X appearing in the peptide: γ-Glu-X-Gly may be one of the foregoing amino acids or derivatives thereof, but it can be an amino acid or a derivative thereof other than cysteine (Cys).

Amino acid residues can be expressed in terms of the following abbreviations, respectively:

(1) Gly: Glycine; (2) Ala: Alanine; (3) Val: Valine; (4) Leu: Leucine; (5) Ile: Isoleucine; (6) Met: Methionine; (7) Phe: Phenylalanine; (8) Tyr: Tyrosine; (9) Trp: Tryptophane; (10) His: Histidine; (11) Lys: Lysine; (12) Arg: Arginine; (13) Ser: Serine; (14) Thr: Threonine; (15) Asp: Aspartic Acid; (16) Glu: Glutamic Acid; (17) Asn: Asparagine; (18) Gln: Glutamine; (19) Cys: Cysteine; (20) Pro: Proline; (21) Orn: Ornithine; (22) Sar: Sarcosine; (23) Cit: Citrulline; (24) N-Val (or Nva): Norvaline (2-aminovaleric acid); (25) N-Leu (or Nle): Norleucine; (26) Abu: α-Aminobutyric Acid; (27) Tau: Taurine; (28) Hyp: Hydroxy-proline; (29) t-Leu: tert-Leucine; (30) Cle: Cycloleucine; (31) Aib: α-Amino-isobutyric Acid (2-methylalanine); (32) Pen: L-Penicillamine; (33) allo-Thr: allo-threonine; (34) allo-Ile: allo-Isoleucine.

Furthermore, the term "amino acid derivative" can mean various kinds of derivatives of the foregoing amino acids and such derivatives can include, for instance, special amino acids, artificially synthesized amino acids, amino alcohols, or the foregoing amino acids in which the terminal carbonyl groups and/or amino groups, or the side chains thereof such as thiol group of cysteine are substituted with a variety of substituents. Specific examples of such substituents can include alkyl groups, acyl groups, hydroxyl group, amino groups, alkylamino groups, nitro groups, sulfonyl groups and various kinds of protective groups. Specific examples of the foregoing amino acid derivatives include N-γ-nitroarginine: Arg (NO₂); S-nitrocysteine: Cys (SNO); S-methylcysteine: Cys (S-Me); S-allylcysteine: Cys (S-allyl); valineamide: Val-NH₂; and valinol (2-amino-3-methyl-1-butanol): Val-ol. In this connection, the peptide: γ-Glu-Cys (SNO)-Gly can be represented by the following structural formula, and the symbol (O) appearing in the foregoing formulas: γ-Glu-Met (O) and γ-Glu-Cys (S-Me) (O) can mean that these peptides each have a sulfoxide structure. The symbol (γ-) appearing in γ-Glu can mean that another amino acid residue is bound to the glutamic acid through the carboxyl group present on the γ-position of the latter.

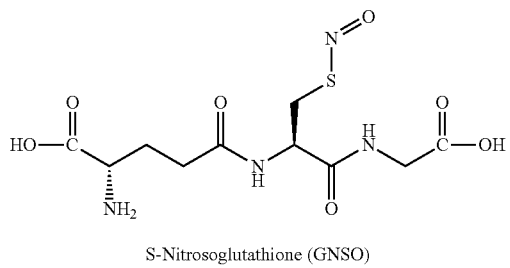 [SMILES: N[C@@H](CCC(=O)N[C@@H](CSN=O)C(=O)NCC(=O)O)C(=O)O]

S-Nitrosoglutathione (GNSO)

The lanthionine derivatives and the foregoing amino acids or peptides used in combination with the lanthionine derivatives can, if any, be commercially available ones. Moreover, they may likewise be prepared, if necessary, according to any known method such as (1) a chemical preparation method or (2) a method for the preparation thereof while using an enzyme, with the chemical synthesis method being more convenient. When chemically synthesizing the lanthionine derivative and the amino acid or peptide used in combination therewith, the peptide may be semi-synthesized or synthesized using a peptide-synthesis device. Examples include the solid phase peptide synthesis method as the foregoing chemically synthesizing method. The peptide synthesized according to the foregoing method can be purified by the usual technique such as the ion-exchange chromatography technique, the reversed phase high performance liquid chromatography technique, or the affinity chromatography technique. Such a solid phase peptide synthesis method and the subsequent peptide purification method have been well known in this art.

Furthermore, when preparing the lanthionine derivative and the amino acid or peptide used in combination therewith through a reaction while making use of an enzyme, the lanthionine derivative and the amino acid or peptide can be prepared according to, for instance, the method disclosed in the pamphlet of the published International Patent Application No. WO 2004/011653. In other words, an amino acid or a dipeptide whose terminal carboxyl group is converted into its ester or amide form is reacted with another amino acid which is in its free state, such as an amino acid whose carboxyl group is protected, in the presence of a peptide-production enzyme, and then the resulting dipeptide or tripeptide is purified to thus give the desired product. The peptide-production enzymes usable herein include, for instance, a culture of a microorganism having an ability to produce an intended peptide; the cell bodies of the microorganism isolated from the culture or a product obtained by treating the cell bodies of the microorganism; or the peptide-production enzyme derived from the microorganism.

Moreover, the peptides can sometimes present in plants such as vegetables and fruits, microorganisms such as yeast, and other naturally occurring substances, in addition to those synthesized according to the foregoing enzymatically synthesizing and chemically synthesizing methods. If they are naturally occurring, it is also possible to extract them from the naturally occurring substance and to use the same.

The kokumi-imparting agent or the kokumi-imparting composition can be used as a seasoning without being subjecting to any further treatment, or after blending the same with a carrier acceptable as an ingredient for foods and beverages and/or other seasoning ingredients. Examples of such other seasoning ingredients include flavor, saccharides, sweeteners, edible fibers, vitamins, amino acids such as sodium glutamate (MSG), nucleic acids such as inosine monophosphate (IMP), inorganic salts such as sodium chloride, and organic acids such as citric acid, as well as a variety of yeast extracts.

The lanthionine derivative and the amino acid or peptide used in combination therewith may be in the form of salts. When the lanthionine derivative and the amino acid or peptide used in combination can form salts, it is sufficient that the salts are pharmaceutically acceptable and edible, and specific examples of such salts include ammonium salts, salts with alkali metals such as sodium and potassium, salts with alkaline earth metals such as calcium and magnesium, aluminum salts, zinc salts, salts with organic amines such as triethylamine, ethanolamine, morpholine, pyrrolidine, piperidine, piperazine and dicyclo-hexylamine, and salts with basic amino acids such as arginine and lysine, for the acidic groups of the foregoing derivative and amino acid or peptide such as carboxyl group. Moreover, specific examples of such salts include salts with inorganic acids such as hydrochloric acid, sulfuric acid, phosphoric acid, nitric acid and hydrobromic acid, salts with organic carboxylic acids such as acetic acid, citric acid, benzoic acid, maleic acid, fumaric acid, tartaric acid, succinic acid, tannic acid, butyric acid, hibenzoic acid, pamoic acid, enanthic acid, decanoic acid, theoclic acid, salicylic acid, lactic acid, oxalic acid, mandelic acid and malic acid, and salts with organic sulfonic acids such as methanesulfonic acid, benzenesulfonic acid and p-toluene-sulfonic acid, for the basic groups of the foregoing derivative and amino acid or peptide.

The lanthionine derivative, the kokumi-imparting agent, the food composition, or the kokumi-imparting composition can be used in any form such as a dry powdery form, a paste, or a solution without any restriction in the physical properties thereof.

The lanthionine derivative, the kokumi-imparting agent, the food composition, or the kokumi-imparting composition according to the present invention can be incorporated into a variety of foods and beverages such as a food, a beverage, and a seasoning.

When incorporating the lanthionine derivative, the kokumi-imparting agent, the food composition, or the kokumi-imparting composition into a variety of foods and beverages such as a food, a beverage, and a seasoning, the final amount of the lanthionine derivative and those of the amino acids or the peptides used in combination with the former are not restricted to particular amounts, inasmuch as they can show the desired effect, but the amount of the lanthionine derivative and/or that of the amino acid or the peptide each range from about 10 ppb to about 99.9% by mass, about 0.05 ppm to about 99.9% by mass, or about 0.1 ppm to about 99.9% by mass, respectively, on the basis of the total mass of the food, beverage or seasoning or the like.

It is also possible to incorporate other additives acceptable for foods and beverages such as any solid or liquid carrier and appropriate seasoning ingredients, into a variety of foods and beverages such as a food, a beverage, and a seasoning, which can include the lanthionine derivative, the kokumi-imparting agent, the food composition, or the kokumi-imparting composition, incorporated into the same.

Examples of the foregoing carriers can include glucose, lactose, sucrose, starch, mannitol, dextrin, fatty acid glycerides, polyethylene glycol, hydroxyethyl starch, ethylene glycol, polyoxyethylene sorbitan fatty acid esters, gelatin, albumin, amino acids, water and physiological saline.

The foregoing seasoning ingredients are not restricted, and may be any known in this art, but specific examples thereof may be those already described above.

The contents of the foregoing carriers and other seasoning ingredients are not restricted to any particular range.

Among the foregoing seasoning ingredients, the yeast extract may be any one and it is not limited in the cell bodies from which it is derived, the conditions for the cultivation thereof and the methods for the extraction thereof and the methods for the treatment of the same. Moreover, the yeast extract can be subjected to any treatment, for instance, heat-treatment, treatment with an enzyme, concentration treatment and/or pulverization treatment.

The present invention will now be described in more detail below with reference to the following non-limiting Examples.

EXAMPLES

Example 1

Synthesis of Compound 1

(Fmoc-L-Cys-Ot-Bu)$_2$ (N,N'-difluorenyl-methoxycarbonyl-L-cystine di-t-butyl ester, 4.81 mmol) was dissolved in a mixed solvent of tetrahydrofuran (58.5 mL) and water (1.5 mL). Then, tributyl phosphine (5.28 mmol) was added to the resulting solution and cooled with ice, and the temperature of the resulting mixture (reaction liquid) was brought back to room temperature, followed by stirring of the same for 4 hours. The reaction liquid was cooled and then a 10% aqueous solution of citric acid (60 mL) was added to the reaction liquid. The temperature of the resulting cloudy liquid was brought back to room temperature and the liquid was extracted with ethyl acetate (60 mL). The organic phase thus obtained was washed with 60 mL of an aqueous common salt solution and then concentrated to thus give an oily residue. The oily residue was purified using a silica gel column (n-hexane-ethyl acetate) to thus obtain Compound 1 as an oily product.

Yield: 97%.
ESI MS m/z 422.4 (M+Na)$^+$.
$^1$H NMR (400 MHz, CDCl$_3$) δ: 1.50; (9H, s), 2.99; (2H, m), 4.23; (1H, t, J=6.8 Hz), 4.41; (2H, m), 4.54; (1H, m), 5.68; (1H, d, J=7.2 Hz), 7.32; (2H, m), 7.41; (2H, t, J=7.2 Hz), 7.61; (2H, d, J=7.6 Hz), 7.77; (2H, d, J=7.2 Hz).

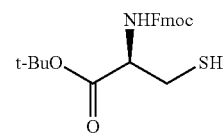

Example 2

Synthesis of Compound 2

Compound 1 (6.04 mmol) prepared in Example 1 was dissolved in dehydrated dimethylformamide (60 mL), followed by the addition to the resulting solution of Boc-iodo-D-Ala-OMe (N-t-butoxycarbonyl-3-iodo-D-alanine methyl ester) (6.20 mmol) and then cesium carbonate (6.02 mmol), and the resulting mixture (reaction liquid) was subsequently stirred at room temperature over night. The reaction liquid was then cooled, followed by the addition of a 10% aqueous citric acid solution (50 mL) and water (30 mL), the extraction of the mixture with ethyl acetate (60 mL), and the extraction, for a second time, of the aqueous phase with ethyl acetate (60 mL). The organic phases thus obtained were combined together, the combined organic phase was washed, in order, with a 10% aqueous citric acid solution (50 mL) and an aqueous common salt solution (50 mL), and then the organic phase was concentrated. The resulting oily residue was purified using a silica gel column (n-hexane-ethyl acetate) to thus give Compound 2 as an oily product.

Yield: 66%.
ESI MS m/z: 601.2 (M+H)$^+$
$^1$H NMR (400 MHz, CDCl$_3$) δ: 1.45; (9H, s), 1.49; (9H, s), 3.01; (4H, m), 3.73; (3H, s), 4.24; (1H, t, J=7.2 Hz), 4.39; (2H, d, J=7.2 Hz), 4.48-4.55; (2H, m), 5.37; (1H, brd, J=6.8 Hz), 5.80; (1H, brd, J=6.8 Hz), 7.32; (2H, m), 7.40; (2H, t, J=7.2 Hz), 7.63; (2H, m), 7.77; (2H, d, J=7.6 Hz).

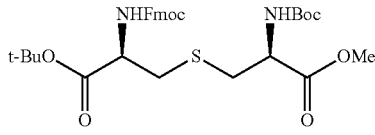

2

Example 3

Synthesis of Compound 4

Step 1: Compound 2 (4.01 mmol) prepared in Example 2 was dissolved in 70 mL of dichloromethane, and then trifluoroacetic acid (70 mL) was added to the resulting solution. The resulting mixture (reaction liquid) was stirred at room temperature for one hour, and the reaction liquid was concentrated to thus give a residue containing Compound 3. The residue containing Compound 3 was used in the subsequent step without any pretreatment assuming that the yield of the compound is 100%.

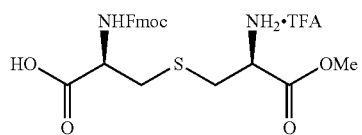

3

Step 2: Dehydrated dimethylformamide (60 mL) was added to Compound 3 (equivalent to 4.01 mmol) prepared in the foregoing step 1 with ice cooling to give a uniform solution and then diisopropylethylamine (8.04 mmol) was dropwise added to the uniform solution. The temperature of the resulting mixture (reaction liquid) was brought back to room temperature, carbonyl bis-imidazole (8.10 mmol) was added to the mixture and the reaction liquid was then stirred overnight without any treatment. A 10% aqueous citric acid solution (50 mL) was added to the reaction liquid under cooling and stirring conditions, the temperature of the reaction liquid was brought back to room temperature, the reaction liquid was then extracted with ethyl acetate (100 mL), the aqueous phase was further extracted with ethyl acetate, and the resulting organic phases were combined together. This organic phase was washed twice with a 10% aqueous citric acid solution (50 mL×2) and then once with an aqueous common salt solution, followed by the concentration of the organic phase to give an oily residue. The resulting residue was purified using a silica gel column (n-hexane-ethyl acetate) to thus give Compound 4 as an oily product.

Yield: 39% (overall yield for the foregoing two steps).

ESI MS m/z 448.5 (M+Na)+

$^1$H NMR (400 MHz, CDCl$_3$) δ 2.71; (1H, dd, J=9.2, 14.4 Hz), 2.78-2.90; (2H, m), 3.02; (1H, d, J=14.4 Hz), 3.86; (3H, s), 4.20; (1H, t, J=6.8 Hz), 4.40; (2H, d, J=6.8 Hz), 4.56; (1H, dd, J=5.6, 9.2 Hz), 4.68; (1H, m), 6.30; (1H, d, J=5.6 Hz), 7.32; (2H, t, J=7.6 Hz), 7.40; (2H, t, J=7.6 Hz), 7.60; (2H, d, J=7.6 Hz), 7.77; (2H, d, J=7.6 Hz).

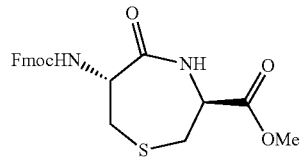

4

Example 4

Synthesis of Compound 6

Step 1: To Compound 4 (1.54 mmol) prepared in Example 3, a 10% morpholine-dimethylformamide solution (14 mL) was added and the resulting mixture (reaction liquid) was stirred at room temperature for 30 minutes. The reaction liquid was then concentrated to give a residue containing Compound 5. The residue was used in the subsequent reaction without any pretreatment assuming that the yield of Compound 5 is 100%.

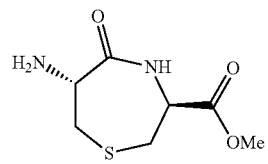

5

Step 2: Boc-L-Glu-OtBu (N-t-butoxycarbonyl-L-glutamic acid α-t-butyl ester) (1.70 mmol) was dissolved in dehydrated dimethylformamide (9 mL), and HOBt.H$_2$O (1-hydroxybenzotriazole hydrate) (1.85 mmol) and WSC.HCl (1-(3-dimethyl-aminopropyl)-3-ethoxycarbodiimide hydrochloride) (1.90 mmol) were added to the resulting solution. Then, the resulting mixture was stirred at room temperature for 15 minutes. To the mixture, Compound 5 (equivalent to 1.54 mmol) suspended in dimethylformamide (20 mL) was added, and the reaction was continued at room temperature overnight. After the reaction liquid was concentrated, there were then added, to the resulting residue, ethyl acetate (50 mL) and water (50 mL) to thus separate the mixture into phases and to remove the organic phase and the aqueous phase was further extracted with ethyl acetate (50 mL). The organic phases were combined, washed with an aqueous sodium bicarbonate solution (50 mL) and an aqueous common salt solution (50 mL), followed by the concentration of the organic phase to give a paste-like residue. The resulting paste-like residue was purified using a silica gel column (n-hexane-ethyl acetate) to thus give Compound 6 as an oily product.

Yield: 81% (overall yield for the foregoing two steps).

ESI MS m/z 490.0 (M+H)+

$^1$H NMR (300 MHz, CDCl$_3$) δ 1.44; (9H, s), 1.46; (9H, s), 1.90; (1H, m), 2.17; (1H, m), 2.32; (2H, m), 2.60; (1H, dd, J=10.5, 14.1 Hz), 2.92-2.98; (2H, m), 3.18; (1H, dd, J=6.0, 14.7 Hz), 3.84; (3H, s), 4.46; (1H, m), 4.80; (1H, m), 5.19; (1H, d, J=8.1 Hz), 6.32; (1H, d, J=8.1 Hz), 7.09; (1H, brs).

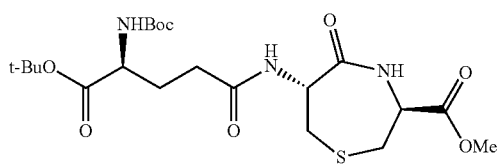

6

Example 5

Synthesis of Compounds 8a and 8b

Step 1: Compound 6 (1.25 mmol) prepared in Example 4 was dissolved in tetrahydrofuran (30 mL), and a 0.2 M aqueous lithium hydroxide solution (2.50 mmol) was added to the resulting solution under ice-cooling and stirring conditions. After 30 minutes, the resulting mixture was neutralized to a pH value of about 6 using a 10% aqueous citric acid solution. The temperature of the mixture (reaction liquid) was brought back to room temperature, the reaction liquid was then concentrated and the concentrate was extracted three times with ethyl acetate (20 mL×3) to obtain an extract or an organic phase. The aqueous phase was further extracted thrice with ethyl acetate (20 mL×3), the resulting organic phases were combined together, washed with an aqueous common salt solution (10 mL) and then concentrated to give Compound 7. The resulting Compound 7 was used in the subsequent reaction without any pretreatment on the assumption that the yield thereof was assumed to be 100%.

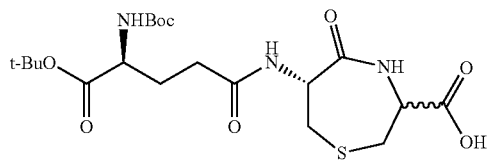

7

Step 2: To Compound 7 (corresponding to 1.25 mmol) prepared in the foregoing step 1, a 4N hydrochloric acid/dioxane solution (25 mL) was added, followed by the reaction of these components at room temperature overnight and the reaction liquid was then concentrated. The resulting paste-like residue was purified using a strong acid type ion-exchange resin (Amberlite IRA 400 OH AG) to thus obtain two fractions. A part of the fraction eluted earlier was further purified by the reversed phase preparative HPLC (column: Develosil RPAQUEOUS-AR-5; mobile phase: linear gradient of water/acetonitrile containing 0.1% formic acid) to thus give Compound 8a as a wheat gluten-like product. On the other hand, the fraction eluted later was concentrated to give a white solid. The white solid was dissolved in water and the resulting aqueous solution was lyophilized to give a residue. The resulting residue was washed with water according to slurry-washing technique to thus give Compound 8b as a white solid.

Compound 8a

ESI MS m/z 318.3 (M–H)⁻

$^1$H NMR (600 MHz, D$_2$O) δ 2.13 (2H, m), 2.50; (2H, t, J=7.8 Hz), 2.64; (1H, d, J=15.0 Hz), 2.83; (1H, dd, J=10.8, 15.0 Hz), 3.02; (1H, dd, J=2.4, 15.0 Hz), 3.15; (1H, dd, J=5.4, 15.0 Hz), 3.83; (1H, t, J=6.0 Hz), 4.55; (1H, dd, J=2.4, 5.4 Hz), 4.91; (1H, dd, J=2.4, 10.8 Hz).

Compound 8b

Yield: 26% (overall yield for the foregoing two steps)

ESI MS m/z 318.0 (M–H)⁻

$^1$H NMR (600 MHz, D$_2$O) δ 2.12; (2H, m), 2.48; (2H, t, J=7.2 Hz), 2.72; (1H, d, J=14.4 Hz), 2.76; (1H, dd, J=10.2, 14.4 Hz), 2.89; (1H, dd, J=9.6, 14.4 Hz), 3.05; (1H, d, J=14.4 Hz), 3.78; (1H, t, J=6.0 Hz), 4.42; (1H, d, J=9.6 Hz), 4.91; (1H, d, J=10.2 Hz).

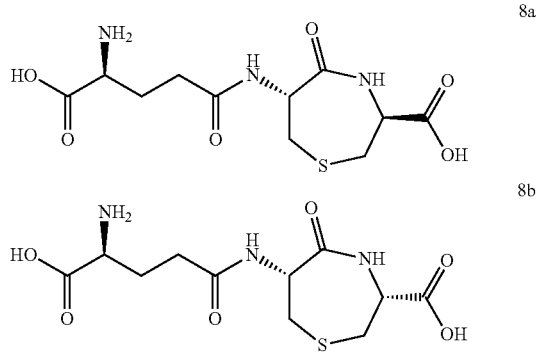

Example 6

Synthesis of Compound 9

D-cystine (5.20 mmol) was dissolved in a 60% aqueous perchloric acid solution (2.1 mL), then, t-butyl acetate (12.6 mL) was dropwise added to the resulting solution, the mixture (reaction liquid) was stirred at room temperature for two days, the reaction liquid was ice-cooled and the pH value of the liquid was adjusted to a level of about 11 using a 4N aqueous sodium hydroxide solution. The temperature of the reaction liquid was brought back to room temperature, the reaction liquid was extracted 6 times with ethyl acetate (50 mL) and the resulting organic phases were combined together, followed by the drying of the combined organic phase over sodium sulfate and the subsequent concentration of the organic phase to thus give Compound 9 as an oily product.

Yield: 72%.

ESI MS m/z 353.2 (M+H)⁺

$^1$H NMR (400 MHz, CDCl$_3$) δ: 1.48; (18H, s), 2.88; (2H, dd, J=8.0, 13.2 Hz), 3.14; (2H, dd, J=4.4, 13.2 Hz), 3.69; (2H, dd, J=4.4, 8.0 Hz).

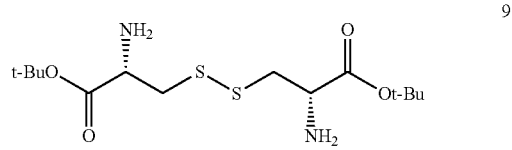 [SMILES: CC(C)(C)OC(=O)[C@H](N)CSSC[C@@H](N)C(=O)OC(C)(C)C]

Example 7

Synthesis of Compound 10

Compound 9 (3.70 mmol) prepared in Example 6 was dissolved in tetrahydrofuran (40 mL), and then Fmoc-OSc (N-(9-fluorenyl-methoxy-carbonyloxy)-succinimide) (7.40 mmol) was added to the resulting solution. This reaction liquid was ice-cooled, N-methyl-morpholine (7.46 mmol) was dropwise added to the reaction liquid and the mixture was stirred overnight without any treatment. To this reaction liquid, ethyl acetate (50 mL) and a 10% aqueous citric acid solution (25 mL) were added to thus separate the mixture into different phases to obtain an organic phase. The resulting organic phase was further washed twice with a 10% aqueous citric acid solution (25 mL) and an aqueous common salt solution (25 mL), and then concentrated to give a slurry-like residue. The slurry-like residue was purified using a silica gel column (n-hexane-ethyl acetate) to thus obtain Compound 10 as a white solid.

Yield: 54%.

ESI MS m/z 819.1 (M+Na)$^+$ $^1$H NMR (400 MHz, CDCl$_3$) δ 1.48; (18H, s), 3.21; (4H, m), 4.20; (2H, m), 4.35; (4H, m), 4.56; (2H, m), 5.72; (2H, d, J=7.2 Hz), 7.28; (4H, m), 7.38; (4H, m), 7.28; (4H, d, J=7.6 Hz), 7.28; (4H, d, J=7.6 Hz).

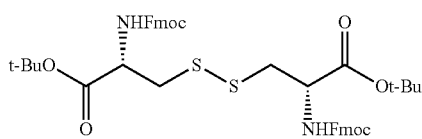

10

Example 8

Synthesis of Compounds 8c and 8d

The same procedures used in Examples 1 to 5 were repeated except for using Compound 10 described in Example 7 as a starting material to thus synthesize Compounds 8c and 8d.

Compound 8c

ESI MS m/z 317.9 (M−H)$^-$ $^1$H NMR (600 MHz, D$_2$O) δ: 2.10; (2H, m), 2.44; (2H, m), 2.59; (1H, brd, J=14.4 Hz), 2.79; (1H, dd, J=10.4, 14.4 Hz), 2.98; (1H, dd, J=2.8, 14.8 Hz), 3.11; (1H, dd, J=6.0, 14.8 Hz), 3.80; (1H, t, J=6.0 Hz), 4.50; (1H, dd, J=2.8, 6.0 Hz), 4.81; (1H, dd, J=2.0, 10.4 Hz).

Compound 8d

ESI MS m/z 317.8 (M−H)$^-$ $^1$H NMR (600 MHz, D$_2$O) δ 2.09 (2H, m), 2.43; (2H, m), 2.67; (1H, dd, J=1.6, 14.4 Hz), 2.72; (1H, dd, J=9.6, 14.4 Hz), 2.84; (1H, dd, J=9.6, 14.4 Hz), 3.02; (1H, d, J=14.4 Hz), 3.77; (1H, t, J=6.0 Hz), 4.42; (1H, dd, J=1.6, 9.6 Hz), 4.87; (1H, dd, J=2.4, 9.6 Hz).

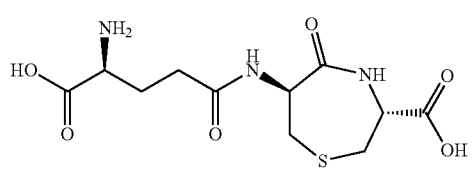

8c

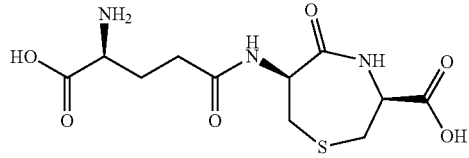

8d

Example 9

Synthesis of Compound 11

To H-D-Asp-OMe (D-aspartic acid α-methyl ester) (6.81 mmol), tetrahydrofuran (14 mL) and water (14 mL) were added to dissolve the former in the latter. To the resulting solution, a solution obtained by dissolving Boc2O (di-t-butyl dicarbonate) (8.38 mmol) in tetrahydrofuran (5 mL), was added to triethylamine (13.63 mmol) and DMAP (N,N-dimethyl-4-aminopyridine) (1.36 mmol), under ice-cooled conditions. The temperature of the mixture (reaction liquid) was brought back to room temperature, the mixture was stirred for 6 hours and the reaction liquid was concentrated to thus remove the tetrahydrofuran. To the remaining reaction liquid, a 1-2N hydrochloric acid solution was added to adjust the pH value thereof to a level of about 2, and then the reaction liquid was extracted with ethyl acetate (50 mL). The resulting organic phase was washed with an aqueous common salt solution (25 mL) and then concentrated to thus give intended Compound 11 as a wheat gluten-like product.

Yield: 76%.

$^1$H NMR (400 MHz, CDCl$_3$) δ 1.48 (9H, s), 2.91; (1H, dd, J=4.4, 8.0 Hz), 3.10; (1H, dd, J=3.6, 8.0 Hz), 3.79; (3H, s), 4.61; (1H, m), 5.52; (1H, brd, J=8.8 Hz).

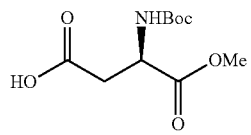

11

Example 10

Synthesis of Compound 13

Step 1: Compound 11 (5.19 mmol) prepared in Example 9 was dissolved in ethyl acetate (21 mL) and then HOSu (N-hydroxy-succinimide) (5.73 mmol) was added to the resulting solution. After the addition of DCC (dicyclohexylcabodiimide) (5.71 mmol) to the mixture with ice-cooling, the temperature of the resulting reaction liquid was brought back to room temperature and the liquid was stirred for 4 hours. The insoluble matter separated out of the reaction liquid was filtered off and the filtrate was concentrated to thus give a gel-like residue containing Compound 12. The resulting residue was used in the subsequent reaction without any pretreatment assuming that the yield of Compound 12 is 100%.

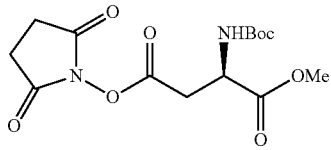

12

Step 2: A mixed liquid containing tetrahydrofuran (20 mL) and water (5 mL) was ice-cooled and then sodium boron hydride (9.47 mmol) was added to the mixed liquid, followed by the stirring of the resulting mixture for 10 minutes and the subsequent dropwise and gradual addition of a solution of Compound 12 (equivalent to 5.19 mmol) prepared above in tetrahydrofuran (20 mL). After 10 minutes, a saturated aqueous ammonium chloride solution (12 mL) was added to the foregoing reaction system and then the temperature of the reaction system was brought back to room temperature. The reaction system was extracted thrice with ethyl acetate (30 mL×3) to obtain an organic phase, the latter was then concentrated and the resulting residue was purified using a silica gel column (dichloromethane-methanol) to thus obtain Compound 13 as a gel-like product.

Yield: 67% (overall yield for the foregoing 2 steps)

$^1$H NMR (400 MHz, CDCl$_3$) δ: 1.47; (9H, s), 1.63; (1H, m), 2.17; (1H, m), 3.73; (2H, m), 3.80; (3H, s), 4.50; (1H, m), 5.39; (1H, m).

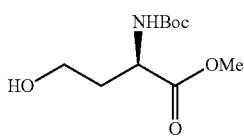

13

Example 11

Synthesis of Compound 14

Compound 13 (3.47 mmol) prepared in Example 10 was dissolved in dehydrated dichloromethane (10 mL) and the resulting solution was then dropwise added to a dehydrated methylene chloride solution (10 mL) of triphenyl-phosphine (4.18 mmol), imidazole (4.17 mmol) and iodine (4.16 mmol). After stirring the mixture (reaction liquid) at room temperature for 2 hours, the reaction liquid was concentrated to obtain a residue and ethyl acetate (35 mL) was added to the resulting residue. After stirring the mixture in the form of a slurry for one hour, the insoluble matter was removed through filtration, and the filtrate was then concentrated to thus give a brown-colored oil. The oil was then purified using a silica gel column (n-hexane-ethyl acetate) to give Compound 14 as an oily product.

Yield: 56%.

$^1$H NMR (400 MHz, CDCl$_3$) δ: 1.47; (9H, s), 2.20; (1H, m), 2.45; (1H, m), 3.20; (2H, t, J=7.6 Hz), 3.79; (3H, s), 4.38; (1H, m), 5.13; (1H, brs).

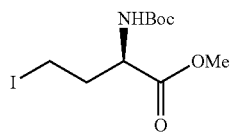

14

Example 12

Synthesis of Compound 15

Fmoc-Cys-Ot-Bu (N-fluorenyl-methoxycarbonyl-L-cysteine t-butyl ester) (1.90 mmol) was dissolved in dehydrated dimethylformamide (10 mL), followed by the addition of a dehydrated dimethylformamide solution (10 mL) of Compound 14 (1.94 mmol) prepared in Example 11 to the resulting solution. Then cesium carbonate (1.92 mmol) was added to the resulting mixture, this mixture (reaction liquid) was stirred at room temperature for 5 hours, and the reaction liquid was separated into phases by the addition of ethyl acetate (20 mL) and a 10% aqueous solution of citric acid (10 mL) to thus obtain an organic phase. The remaining aqueous phase was again extracted with ethyl acetate (20 mL), the organic phases were combined together and then washed with a 10% aqueous solution of citric acid (10 mL) and a saturated aqueous common salt solution (10 mL). The resulting organic phase was concentrated to give an oily residue and the latter was purified using a silica gel column (n-hexane-ethyl acetate) to give Compound 15 as an oily product.

Yield: 62%.

$^1$H NMR (400 MHz, CDCl$_3$) δ 1.45; (9H, s), 1.51; (9H, s), 1.92; (1H, m), 2.12; (1H, m), 2.63; (2H, m), 2.99; (2H, m), 3.74; (3H, s), 4.26; (1H, t, J=7.2 Hz), 4.41; (2H, m), 4.50; (1H, m), 5.17; (1H, br), 7.34; (2H, m), 7.43; (2H, t, J=7.2 Hz), 7.65; (2H, d, J=7.2 Hz), 7.79; (2H, d, J=7.6 Hz).

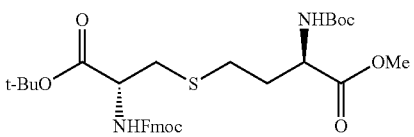

15

Example 13

Synthesis of Compound 16

Step 1: Compound 15 (0.55 mmol) prepared in Example 12 was dissolved in dehydrated dichloromethane (8 mL), trifluoroacetic acid (4 mL) was then added to the solution and the mixture (reaction liquid) was stirred at room temperature for 2 hours. This reaction liquid was concentrated and dehydrated dimethyl-formamide (4 mL) was added to the concentrate and the mixture was distilled off as an azeotropic mixture to thus give a dimethylformamide solution containing Compound 16. The resulting azeotropic mixture was used in the subsequent reaction without any pretreatment assuming that the yield of Compound 16 is 100%.

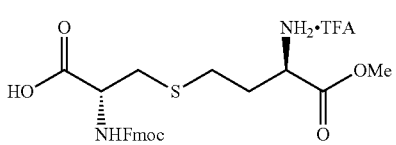

16

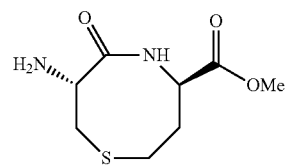

18

Step 2: Additional dehydrated dimethylformamide (24 mL) was added to a dimethylformamide solution containing Compound 16 (equivalent to 0.55 mmol) and to this mixture, PyBOP (benzotriazole-1-yl-oxy-tris-pyrrolidino-phosphonium hexafluoro-phosphate) (0.82 mmol) and WSC.HCl (1-(3-dimethylaminopropyl)-3-ethoxycarbodiimide hydrochloride) (0.83 mmol) were added, with stirring. Then triethylamine (0.65 mmol) was added to the resulting reaction system, followed by the stirring of the reaction system at room temperature for 24 hours and the concentration of the reaction liquid. Water (10 mL) and ethyl acetate (10 mL) were added to another container, the resulting mixed solvent was stirred and the foregoing concentrate of the reaction liquid was added to the mixed solvent. Further, the resulting mixture was washed and extracted with ethyl acetate (10 mL) to thus obtain an organic phase. The remaining aqueous phase was further extracted twice with ethyl acetate (10 mL×2), the organic phases thus obtained were combined together and the combined organic phase was washed with a saturated aqueous sodium bicarbonate solution (10 mL) and a saturated aqueous common salt solution (10 mL). To the white solid obtained after the concentration of the organic phase, ethyl acetate was added to give a slurry, followed by the stirring of the slurry and the removal of the insoluble matter through filtration. The oily residue obtained by the concentration of the filtrate was purified using a silica gel column (n-hexane-ethyl acetate) to give Compound 17 as a white solid.

Yield: 15% (overall yield for the foregoing two steps).

ESI MS m/z 257.5 (M+H)+.

Step 2: Boc-Glu-Ot-Bu(N-t-butoxycarbonyl-L-glutamic acid α-t-butyl ester) (0.096 mmol) was dissolved in dehydrated dimethylformamide (1 mL), and then HOBt.H$_2$O (1-hydroxybenzotriazole hydrate) (0.12 mmol) and WSC.HCl (1-(3-dimethylaminopropyl)-3-ethoxycarbodiimide hydrochloride) (0.12 mmol) were added to the resulting solution, followed by the stirring of the resulting mixture (reaction liquid) at room temperature for 10 minutes. To this reaction liquid, there was added a dehydrated dimethylformamide solution (2 mL) of Compound 18 (equivalent to 0.08 mmol), followed by the stirring of the resulting mixture at room temperature overnight. To the residue obtained by the concentration of the reaction liquid, there were added ethyl acetate (20 mL) and water (10 mL) to separate the liquid into phases. The resulting organic phase was washed with a saturated aqueous sodium bicarbonate solution (10 mL) and a saturated aqueous common salt solution (10 mL) and then concentrated. The resulting residue was purified using a silica gel column (n-hexane-ethyl acetate) to thus give Compound 19 as a wheat gluten-like product.

Yield: 90%.

$^1$H NMR (400 MHz, CDCl$_3$) δ 1.46; (9H, s), 1.48; (9H, s), 1.88; (1H, m), 2.40-2.15; (5H, m), 2.50; (1H, m), 2.78; (1H, dd, J=10.0, 14.4 Hz), 3.09; (1H, dd, J=4.8, 15.6 Hz), 3.37; (1H, dd, J=4.8, 14.4 Hz), 3.68; (1H, t, J=4.8 Hz), 3.79; (3H, s), 4.18; (1H, m), 4.51; (1H, m), 5.01; (1H, m), 5.20; (1H, brd, J=6.8 Hz).

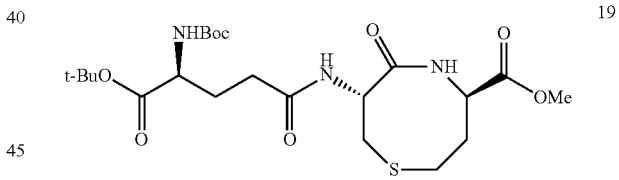

19

Example 15

Synthesis of Compound 21

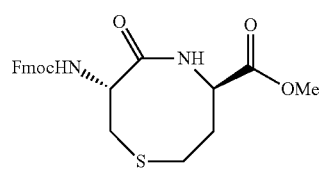

17

Example 14

Synthesis of Compound 19

Step 1: To Compound 17 (0.08 mmol) prepared in Example 13, a 5% morpholine/dimethylformamide solution (0.70 mL) was added, the mixture (reaction liquid) was stirred at room temperature for one hour and the reaction liquid was then concentrated to give a solution containing compound 18. The resulting solution was used in the subsequent reaction without any pretreatment assuming that the yield of Compound 18 is 100%.

Step 1: Compound 19 (0.092 mmol) prepared in Example 14 was dissolved in tetrahydrofuran (1.84 mL), a 0.2N aqueous lithium hydroxide solution (0.18 mmol) was added to the resulting solution under ice-cooling, the temperature of the mixture was brought back to room temperature and the mixture (reaction liquid) was stirred at that temperature for one hour. After confirming the disappearance of the raw materials by the TLC technique, a 0.2N hydrochloric acid solution was added to the reaction liquid to control the pH value thereof to a weakly acidic level, followed by the concentration of the reaction liquid to remove the tetrahydrofuran. The remaining liquid was extracted three times with ethyl acetate (10 mL×3) and the resulting organic phase was washed with a saturated aqueous common salt solution. The organic phase was concentrated to give wheat gluten-like Compound 20 as a diastereomer mixture. The resulting diastereomer mixture was used in the subsequent reaction without any pretreatment on the assumption that the yield thereof was assumed to be 100%.

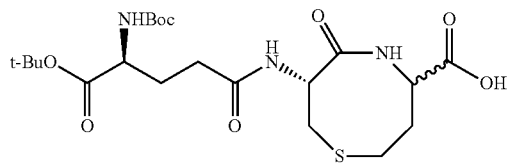

20

Step 2: To Compound 20 (equivalent to 0.092 mmol) prepared in the foregoing step 1, a 4N hydrochloric acid/dioxane solution (1.8 mL) was added, and the mixture (reaction liquid) was stirred at room temperature overnight. The residue obtained by the concentration of the reaction liquid was dissolved in water and the aqueous solution was passed through an anionic ion-exchange resin (Amberlite IRA 400 OH AG). After washing the resin with ion-exchanged water, it was eluted with 1 to 3N acetic acid solution, followed by the lyophilization of the eluate to thus give Compound 21 as a diastereomer mixture.

Yield: 56% (as the overall yield for the foregoing two steps).

ESI MS m/z 334.0 (M+H)+; $^1$H NMR (400 MHz, D$_2$O) δ 2.07; (2H, m), 2.42; (2H, m), 2.86-3.17; (2H, m), 3.75; (1H, t, J=6.0 Hz), 4.27~4.41; (1H, m), 4.75~5.24; (1H, m).

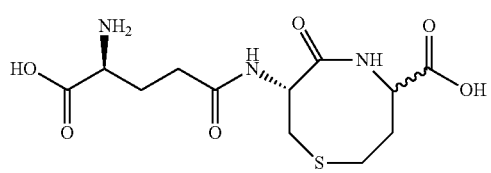

21

Example 16

Synthesis of Compound 22

(Boc-L-Cys-OH)$_2$ (N,N'-di-t-butoxycarbonyl-L-cystine) (2.51 mmol) was dissolved in tetrahydrofuran (29.2 mL) and water (0.8 mL), and tributyl-phosphine (2.76 mmol) was then added to the solution under ice-cooled conditions. The temperature of this reaction liquid was brought back to room temperature, followed by the stirring of the reaction liquid for one hour at that temperature and the concentration of the reaction liquid. To the resulting residue, ethyl acetate (20 mL) and a 10% aqueous citric acid solution (10 mL) were added to fractionate the residue and the resulting organic phase was washed with a saturated aqueous common salt solution (20 mL). The organic phase was concentrated and the resulting residue was purified using a silica gel column (n-hexane-ethyl acetate) to thus give Compound 22 as an oily product.

Yield: 99%.

ESI MS m/z 220.1; (M−H)−; $^1$H NMR (400 MHz, CDCl$_3$) δ: 5.47; (1H, brs), 4.65; (1H, brs), 3.09-2.97; (2H, m), 1.48; (9H, s).

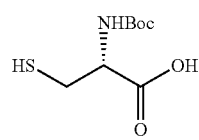

22

Example 17

Synthesis of Compound 23

Compound 18 (4.97 mmol) prepared in Example 14 (step 1) and acetic acid anhydride (49.90 mmol) were combined, the resulting mixture was ice-cooled, and a solution of potassium hydrogen carbonate (5.93 mmol) in water (2.4 mL) was dropwise added to the ice-cooled mixture. The temperature of the reaction system (the foregoing mixture) was brought back to room temperature, followed by the stirring of the reaction system for 2 hours and the addition of water (5 mL) and ethyl acetate (20 mL) for the extraction, which resulted in the formation of an aqueous phase and an organic phase. The resulting aqueous phase was further extracted with ethyl acetate (20 mL) to give an additional organic phase. These organic phases were combined together and then washed with a saturated aqueous common salt solution (5 mL). The combined organic phase was concentrated and the resulting residue was purified using a silica gel column (n-hexane-ethyl acetate) to thus give Compound 23 as a wheat gluten-like product.

Yield: 76%.

ESI MS m/z 261.9; (M−H)−; $^1$H NMR (400 MHz, CDCl$_3$) δ 5.33; (1H, d, J=6.4 Hz), 4.53; (1H, m), 3.47; (1H, dd, J=4.0, 14.0 Hz), 3.34; (1H, dd, J=6.8, 14.0 Hz), 2.40; (3H, s), 1.48; (9H, s).

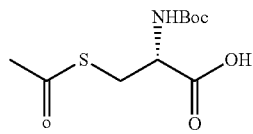

23

Example 18

Synthesis of Compound 24

Compound 23 (3.76 mmol) prepared in Example 17 was dissolved in dehydrated dimethylformamide (30 mL), followed by the addition of HOBt.H2O (1-hydroxybenzotriazole hydrate) (4.14 mmol) and CMC (1-cyclohexyl-3-(2-morphorinoethyl) carbodiimide metho-p-toluene-sulfonate) (4.13 mmol) to the resulting solution and the stirring of the resulting mixture at room temperature for 15 minutes. Thereafter, L-Thr-OMe.HCl (L-threonine methyl ester.HCl) (3.77 mmol) and triethylamine (3.80 mmol) were added to the mixture and the resulting mixture (reaction liquid) was stirred at room temperature for 2 hours. The reaction liquid was concentrated, and water (20 mL) and ethyl acetate (40 mL) were added to the resulting residue to fractionate the same and to obtain an organic phase. The organic phase was washed with an aqueous sodium bicarbonate solution (20 mL) and a saturated aqueous common salt solution (20 mL) and then the organic phase was concentrated. The resulting residue was purified using a silica gel column (dichloromethane-methanol) to thus obtain Compound 24 as a white solid.

Yield: 74%.

ESI MS m/z 401.3; (M+Na)+; $^1$H NMR (400 MHz, CDCl$_3$) δ 7.14; (1H, d, J=7.6 Hz), 5.37; (1H, d, J=7.2 Hz), 4.60; (1H, dd, J=2.8, 8.8 Hz), 4.37; (2H, m), 3.80; (3H, s), 3.39; (1H, dd, J=4.4, 14.0 Hz), 3.24; (1H, dd, J=8.0, 14.0 Hz), 2.40; (3H, s), 1.47; (9H, s), 1.24; (3H, d, J=6.4 Hz).

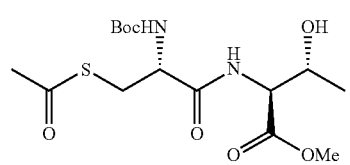

24

Example 19

Synthesis of Compounds 25a and 25b

Compound 24 (4.20 mmol) prepared in Example 18 was dissolved in dehydrated dichloromethane (5 mL), and then diisopropyl-ethylamine (8.38 mmol) and methanesulfonyl chloride (8.00 mmol) were added to the resulting solution. After stirring the mixture (reaction liquid) at room temperature for an hour and a half, the reaction liquid was concentrated to thus obtain an oily residue. On the other hand, lithium aluminum hydride (33.6 mmol) was added to dehydrated tetrahydrofuran (50 mL) with ice-cooling. Then dehydrated methanol (101.48 mmol) was gradually dropwise added to the mixture. To this reaction liquid, dehydrated tetrahydrofuran (50 mL) was additionally added, and the mixture was further stirred. After 10 minutes, the dehydrated tetrahydrofuran solution (15 mL) containing the residue obtained above was dropwise added to the foregoing separately prepared mixture and this reaction was continued for 2 hours. This reaction liquid was added to a mixed liquid containing ethyl acetate (150 mL) and a 0.5N hydrochloric acid solution (120 mL) in small portions to thus fractionate the reaction liquid. The organic phase thus obtained was washed with a 0.5N hydrochloric acid solution (120 mL) and a saturated aqueous common salt solution (120 mL) and then concentrated. The resulting residue was purified using a silica gel column (n-hexane-ethyl acetate) to thus give two Compounds 25a and 25b, which are isomers relative to each other.

25a: Yield 13%; ESI MS m/z 341.1; (M+Na)+; $^1$H NMR (400 MHz, CDCl$_3$) δ: 6.50; (1H, d, J=5.6 Hz), 6.01; (1H, d, J=5.2 Hz), 4.87; (1H, dd, J=1.2, 6.0 Hz), 4.61; (1H, m), 3.87; (3H, s), 3.30; (1H, m), 2.95; (1H, dd, J=10.0, 14.8 Hz), 2.76; (1H, dd, J=1.2, 14.8 Hz), 1.47; (9H, s), 1.24; (3H, d, J=6.8 Hz).

25b: Yield 20%; ESI MS m/z 341.4; (M+Na)+; $^1$H NMR (400 MHz, CDCl$_3$) δ: 6.05; (1H, d, J=8.8 Hz), 5.99; (1H, brs), 4.63; (1H, m), 4.15; (1H, m), 3.87; (3H, s), 3.48; (1H, m), 2.73; (2H, m), 1.49; (3H, d, J=7.2 Hz), 1.47; (9H, s).

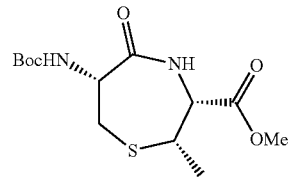

25a

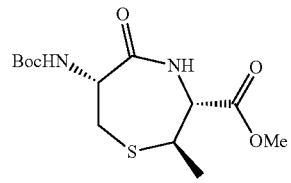

25b

Example 20

Synthesis of Compound 27

Step 1: A 4N hydrochloric acid/dioxane solution (2.26 mL) was added to Compound 25a (0.45 mmol) prepared in Example 19 and the mixture (reaction liquid) was stirred at room temperature overnight. The reaction liquid was then concentrated to thus give a residue containing Compound 26. The resulting residue was used in the subsequent reaction without any pretreatment assuming that the yield of Compound 26 is 100%.

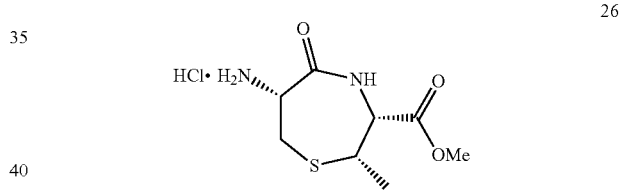

26

Step 2: Boc-Glu-Ot-Bu (N-t-butoxycarbonyl-L-glutamic acid α-t-butyl ester) (0.52 mmol) was dissolved in dehydrated dimethylformamide (4 mL), and HOBt.H$_2$O (1-hydroxybenzotriazole hydrate) (0.65 mmol) and WSC.HCl (1-(3-dimethylamino-propyl)-3-ethoxycarbodiimide hydrochloride) (0.66 mmol) were then added to the resulting solution, and the resulting mixture was stirred at room temperature for 10 minutes. To this mixtue, a dehydrated dimethylformamide solution (2.5 mL) of Compound 26 (equivalent to 0.45 mmol) prepared in the foregoing step 1, and then triethylamine (0.77 mmol) was added, and the mixture (reaction liquid) was stirred at room temperature for 2 hours. The reaction liquid was concentrated, then ethyl acetate (40 mL) and water (20 mL) were added to the resulting residue to fractionate the same and the resulting organic phase was washed with a saturated aqueous sodium bicarbonate (20 mL) and a saturated aqueous common salt solution (20 mL). The organic phase was then concentrated and the resulting residue was purified using a silica gel column (dichloromethane-methanol) to thus give Compound 27.

Yield: 98% (overall yield for these two steps).

ESI MS m/z 526.1; (M+Na)+; $^1$H NMR (400 MHz, CDCl$_3$) δ: 7.02; (1H, m), 6.53; (1H, d, J=6.0 Hz), 5.18; (1H, d, J=7.6 Hz), 4.88; (1H, dd, J=1.2, 5.6 Hz), 4.81; (1H, m), 4.19; (1H, m), 3.87; (3H, s), 3.32; (1H, m), 2.90; (1H, dd, J=10.0, 14.8

Hz), 2.78; (1H, dd, J=2.0, 14.8 Hz), 2.33; (2H, m), 2.21; (1H, m), 1.90; (1H, m), 1.49; (9H, s), 1.46; (9H, s), 1.25; (3H, d, J=6.8 Hz).

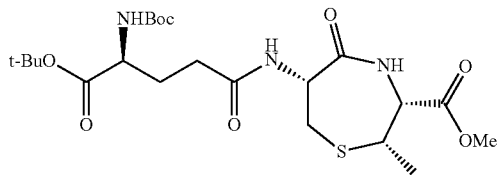

27

Example 21

Synthesis of Compound 29

Step 1: Compound 27 (0.38 mmol) prepared in Example 20 (step 2) was dissolved in tetrahydrofuran (7.6 mL), then a 0.2M aqueous lithium hydroxide solution (0.76 mmol) was added to the solution with ice-cooling and the mixture (reaction liquid) was stirred for 2 hours. Then a 0.5N hydrochloric acid solution was added to the reaction liquid to make the reaction liquid weakly acidic, the temperature of the reaction liquid was brought back to room temperature and then the reaction liquid was concentrated to remove the tetrahydrofuran. The remaining liquid was extracted thrice with ethyl acetate '20 mL×3), the resulting organic phase was washed with a saturated aqueous common salt solution (20 mL) and then concentrated to give Compound 28. The resulting concentrate or residue was used in the subsequent reaction without any pretreatment assuming that the yield of Compound 28 is 100%.

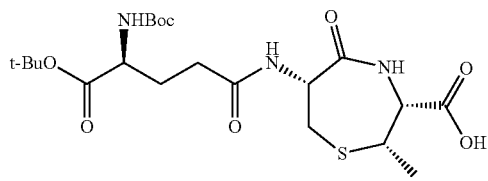

28

Step 2: A 4N hydrochloric acid/dioxane solution (7.2 mL) was added to Compound 28 (equivalent to 0.38 mmol) prepared in the foregoing step 1 and the mixture (reaction liquid) was stirred at room temperature overnight. The reaction liquid was concentrated, the resulting residue was dissolved in water and then the resulting aqueous solution was passed through an anionic ion-exchange resin (Amberlite IRA 400 OH AG). The resin was washed with ion-exchanged water, followed by the elution according to the gradient elution method with 1-3N acetic acid solution and the lyophilization of the resulting eluate to give Compound 29 as a white solid.

Yield: 65% (overall yield for these two steps).

ESI MS m/z 333.6 (M+H)+; $^1$H NMR (400 MHz, $D_2O$) δ: 4.86; (1H, dd, J=2.8, 9.6 Hz), 4.81; (1H, d, J=1.6 Hz), 3.82; (1H, t, J=6.4 Hz), 3.40; (1H, m), 2.95; (1H, dd, J=9.6, 15.2 Hz), 2.60; (1H, dd, J=2.8, 15.2 Hz), 2.46; (2H, t, J=7.2 Hz), 2.08; (2H, m), 1.14; (3H, d, J=7.2 Hz).

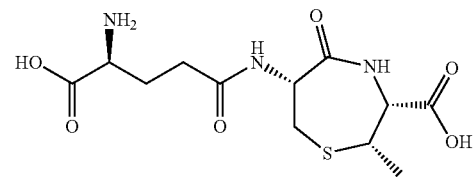

29

Example 22

Synthesis of Compound 35

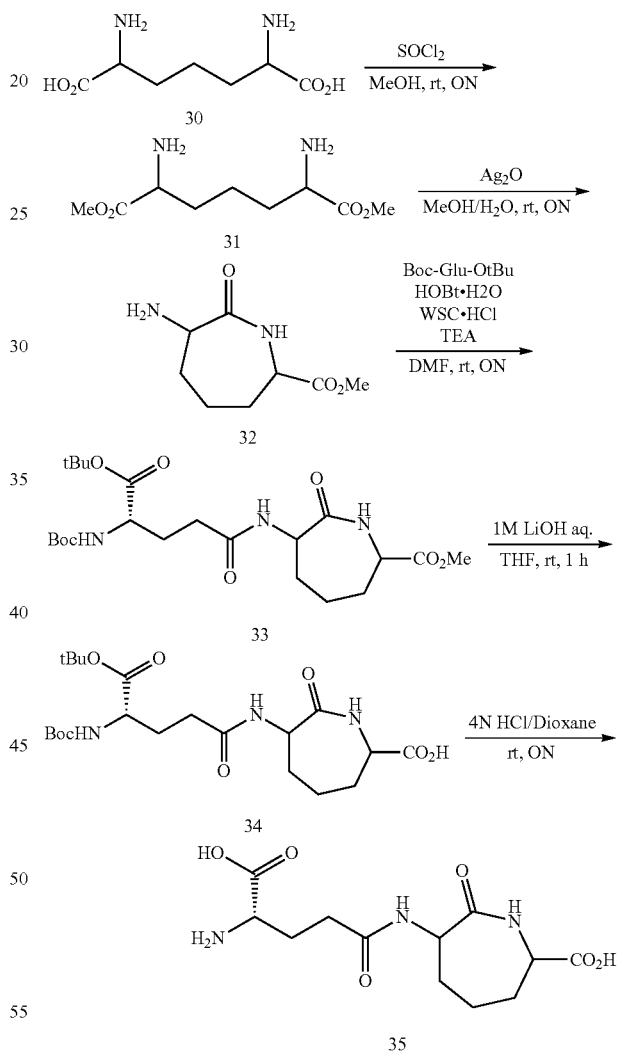

(1) Preparation of Compound 31

2,6-diaminopimelic acid (5.0 g, 26.3 mmol) was dissolved in 42 mL of methanol and then thionyl chloride (4.2 mL, 57.9 mmol) was slowly dropwise added to the resulting solution with ice-cooling. After the completion of the dropwise addition, the temperature of the mixture was allowed to spontaneously raise up to room temperature and the mixture was then stirred overnight. After the completion of the reaction, the solvent was distilled off from the reaction system to obtain Compound 31 in a quantitative yield.

(2) Preparation of Compound 32

Compound 31 (0.582 g, 2.0 mmol) prepared above was dissolved in a mixed solvent containing 10 mL of water and 10 mL of methanol, then silver oxide (0.730 g, 3.2 mmol) was added to the solution and the latter was stirred at room temperature overnight. After the completion of the reaction, the silver oxide was removed by the filtration through celite and the solvent was distilled off from the filtrate to thus give Compound 32 as a crude product.

(3) Preparation of Compound 33

Boc-Glu-Ot-Bu (0.303 g, 1.0 mmol), 1-hydroxybenzotriazole monohydrate (0.169 g, 1.1 mmol), 1-ethyl-3-(3-dimethylaminopropyl) carbodiimide hydrochloride (0.211 g, 1.1 mmol), and Compound 32 (0.205 g, 1.1 mmol) prepared above were dissolved in 5 mL of N,N-dimethylformamide, then triethylamine (0.198 mL, 1.4 mmol) was added to the resulting solution and the resulting mixture (reaction liquid) was stirred at room temperature overnight. After the completion of the reaction, the solvent was distilled off from the reaction liquid, and the remaining liquid was diluted by the addition of ethyl acetate. The diluted liquid was washed twice with a 5% aqueous citric acid solution and then once with a saturated aqueous common salt solution, then washed twice with a 10% saturated aqueous sodium bicarbonate solution and finally once with a saturated aqueous common salt solution. The resulting organic phase was dried over magnesium sulfate, followed by the filtration thereof and the removal of the solvent through distillation to thus give Compound 33 as a crude product.

(4) Preparation of Compound 34

Compound 33 (0.277 g, 0.59 mmol) prepared above was dissolved in 5 mL of tetrahydrofuran, 4 mL of a 1M aqueous lithium hydroxide solution was then added to the resulting solution and the mixture (reaction liquid) was stirred at room temperature for 2 hours. After the completion of the reaction, the pH of the reaction liquid was adjusted to about 2 by the addition of a 1M aqueous hydrochloric acid solution and then ethyl acetate was added to the reaction liquid to extract the same. The resulting organic phase was washed with a saturated aqueous common salt solution, then dried over magnesium sulfate, the latter was removed through filtration and the solvent was distilled off from the filtrate to thus give Compound 34.

(5) Preparation of Compound 35

A 4N hydrochloric acid-dioxane solution was added to Compound 34 (0.181 g, 0.38 mmol) prepared above and the reaction between them was continued at room temperature all the night through. After the completion of the reaction, the solvent was distilled off to give a residue and a part of the residue containing Compound 35 was purified by the reversed phase prepative HPLC (column: Develosil RPAQUEOUS-AR-5, available from NOMURA Chemical Co., Ltd.; mobile phase: linear gradient of water containing 0.1% heptafluorobutyric acid/acetonitrile system) to thus give Compound 35 as a diastereomer mixture.

$^1$H NMR ($D_2O$) δ: 1.41-1.78; (m, 3H), 1.80-1.91; (m, 2H), 1.99-2.03; (m, 1H), 2.08-2.22; (m, 2H), 2.42-2.51; (m, 2H), 3.97-4.02; (m, 1H), 4.31-4.34; (m, 1H), 4.45-4.49; (m, 1H) MS(ESI) m/z: 302.0; (M+1)

Example 23

Preparation of CaSR-Expression Plasmid

The preparation of a CaSR-expression plasmid was carried out according to the following procedures:

There were synthesized synthetic origo DNAs [forward primer (Sequnce No. 3: ACTAATACGACTCACTATAGG-GACCATGGCATTTTATAG-CTGCTGCTGG)] and a reverse primer (Sequence No. 4: TTATGAATTCAC-TACGTTTTCTGTAACAG), to be used in the PCR procedures, on the basis of the DNA sequence registered with NCBI [CaSR (calcium receptor): NM_000388, Sequence Nos. 1 and 2], as a template.

The PCR procedures were carried out using the foregoing primers, and Pfu Ultra DNA Polymerase (available from Stratagene Company) under the following conditions, while using the cDNA derived from human kidney (available from Clontech Company) as a material or a template. In this connection, a series of the replication cycle comprised steps for treating the system at 94° C. for 3 minutes, then at 94° C. for 30 seconds, 55° C. for 30 seconds, and 72° C. for 2 minutes, wherein the latter three steps were repeated over 35 times, and a final step of continuing the reaction at 72° C. for 7 minutes. The electrophoresis procedures were carried out through an electrolyte supported on an agarose gel, followed by the staining of the electrophoresed PCR products with a DNA-staining agent and the subsequent detection, by the irradiation with UV light rays, of whether the intended amplification occurred or not. In addition, the chain lengths of the PCR products were also confirmed by comparing them with those of the DNA markers each having a known size and subjected to the electrophoresis procedures at the same time.

Plasmid vector pBR322 was cut by the restriction enzyme EcoRV (available from Takara Company) and the gene fragments amplified by the foregoing PCR procedures were connected to the plasmid vector at the cut site thereof using Ligation kit (available from Promega Company). Escherichia coli DH5α strain was transformed with this reaction solution, followed by the selection of a transformant which maintained the plasmid capable of undergoing the cloning with the PCR-amplified product and the PCR-amplified product was then confirmed according to the base sequence-analysis of DNA.

This recombinant plasmid was used for the construction or establishment of a human CaSR-expression plasmid hCaSR/pcDNA3.1.

Example 24

Evaluation (1) of CaSR Agonist Activity

293E Cells (EBNA1-expression HEK293 cells, ATCC No. CRL-10852) were cultivated in DMEM/Ham's-F12 (3.15/ml Glucose-containing Dulbecco's modified Eagle medium; available from NAKARAI TESK Company) containing 10% fetal calf serum in the presence of 200 μg/ml of G418 (available from Genetisine Company). The cultured cells were inoculated in F25 flask at a density of $3 \times 10^6$ cells/10 ml, then the content of the flask was allowed to stand for 24 hours in a $CO_2$ incubator (5% $CO_2$, 37° C.), and then the human CaSR-expression plasmid hCaSR/pcDNA3.1 was transfected using a transfection agent Fugene 6 (available from Roche Company). After allowing the flask to stand in a $CO_2$ incubator for 6 to 7 hours, the cells were recovered using 10% fetal calf serum-containing DMEM/Ham's-F12 and then inoculated in each well of a poly-D-lysine coat 96-well plate (BD-Biocoat) at a density of 70,000 cells/well.

After allowing the well plate to stand in a $CO_2$ incubator for 24 hours, the culture medium was removed from each well of the 96-well plate to which the cells had been inoculated, and a solution of $Ca^{2+}$ fluorescent indicator Calcium 4 Assay Kit (available from Molecular Devices Company) in an Assay Buffer (containing 146 mM of NaCl, 5 mM of KCl, 1 mM of $MgSO_4$, 1 mg/ml of Glucose, 20 mM of HEPES (pH 7.2), and 0.75 to 1.25 mM of $CaCl_2$) in an amount of 200 μl/well was added to each well, and each well was allowed to stand at 37° C. for one hour and then at room temperature for 10 minutes to thus make the cells take the indicator.

To each well of the 96-well plate, a solution of a test compound in a 0.1% BSA-containing Assay Buffer in an amount of 50 μl/well was added, and the wells were inspected for any change in the intensity of fluorescent light rays emitted therefrom for 3 minutes using FLEX Station (available from Molecular Devices Company).

Method for the Calculation of $EC_{50}$

The difference (RFU (Max-Min)) between the maximum and minimum intensities of fluorescent light rays observed before and after the addition of the test compound were calculated according to the automatic calculation by the FLEX Station. In this respect, the activity rate of a test compound was calculated, while the RFU (Max-Min) value observed when adding a test compound in a maximum concentration was defined to be 100% and the RFU (Max-Min) value observed when using a 0.1% BSA-containing Assay Buffer free of any added test compound was defined to be 0%, then the curve-fitting was carried out using a software Xfit for spreadsheet or a GraphPad Prism to thus determine each corresponding $EC_{50}$ value as the concentration of each test compound observed at the activity rate of 50%.

Example 25

Evaluation (2) of CaSR Agonist Activity

293E Cells (EBNA1-expression HEK293 cells, ATCC No. CRL-10852) were cultivated in DMEM/Ham's-F12 (3.15/ml Glucose-containing Dulbecco's modified Eagle medium; available from NAKARAI TESK Company) containing 10% fetal calf serum in the presence of 200 μg/ml of G418 (available from Genetisine Company). The cultured cells were inoculated in F25 flask at a density of $3 \times 10^6$ cells/10 ml, then the content of the flask was allowed to stand for 24 hours in a $CO_2$ incubator (5% $CO_2$, 37° C.), and then the human CaSR-expression plasmid: hCaSR/pcDNA3.1 was transfected using a transfection agent Fugene 6 (available from Roche Company). After allowing the flask to stand in a $CO_2$ incubator for 6 to 7 hours, the cells were recovered using 10% fetal calf serum-containing DMEM/Ham's-F12 and then inoculated in each well of a poly-D-lysine coat 384-well plate (BD-Biocoat) at a density of $2 \times 10^6$ cells/well.

After allowing the well plate to stand in a $CO_2$ incubator for 24 hours, the culture medium was removed from each well of the 384-well plate to which the cells had been inoculated, and to each well, a solution of $Ca^{2+}$ fluorescent indicator: Calcium 5 Assay Kit (available from Molecular Devices Company) in an Assay Buffer (containing 146 mM of NaCl, 5 mM of KCl, 1 mM of $MgSO_4$, 1 mg/ml of Glucose, 20 mM of HEPES (pH 7.2), and 0.75 to 1.25 mM of $CaCl_2$, and 2.5 mM of Probenecid (available from SIGMA Company)) in an amount of 40 μl/well was added, and each well was allowed to stand at 37° C. for 45 minutes and then at room temperature for 15 minutes to thus make the cells take the indicator.

To each well of the 384-well plate, a solution of a test compound in a 0.1% BSA-containing Assay Buffer in an amount of 10 μl/well was added, and the wells were inspected for any change in the intensity of the emitted fluorescent light rays for 3 minutes using FLIPR (available from Molecular Devices Company).

Method for the Calculation of $EC_{50}$

The difference (RFU (Max-Min)) between the maximum and minimum intensities of fluorescent light rays observed before and after the addition of the test compound were calculated according to the FLIPR automatic calculation technique. In this respect, the activity rate of a test compound was calculated, while the RFU (Max-Min) value observed when adding a test compound in a maximum concentration was defined to be 100% and the RFU (Max-Min) value observed when using a 0.1% BSA-containing Assay Buffer free of any added test compound was defined to be 0%, then the curve-fitting was carried out using a software Xfit for spreadsheet or a GraphPad Prism to thus determine each corresponding $EC_{50}$ value as the concentration of each test compound observed at the activity rate of 50%.

The following Table 1 shows the results determined according to the foregoing methods (1) and (2):

TABLE 1

| Compound | CaSR Agonist Activity ($EC_{50}$)(μM) |
|---|---|
| γ-Glu-Cys | 0.46 |
| Compound 8a | 14.27 |
| Compound 8b | 0.053 |
| Compound 8c | 19.99 |
| Compound 8d | 1.95 |
| Compound 21 | 1.85 |
| Compound 29 | 0.58 |
| Compound 35 | 0.199 |

All of the compounds described herein showed the desired CaSR agonist activity. Among them, the lanthionine derivative Compound 8b showed an extremely high CaSR agonist activity, which was found to be about 9 times that of γ-Glu-Cys, which had been known to have a CaSR agonist activity.

Example 26

Evaluation of Kokumi-imparting Activity

Compound 8b was inspected for the intensity of its kokumi-imparting activity according to the quantitative organoleptic evaluation test.

The quantitative organoleptic evaluation test was herein carried out according to the following procedures: The intensity of the kokumi-imparting activity were determined in case where a test compound (in an amount ranging from 0.0001 to 0.0005 g/dL was blended with distilled water containing sodium glutamate (0.05 g/dL), inosine monophosphate (inosinic acid) (0.05 g/dL), and sodium chloride (0.5 g/dL). The pH value of the samples used was adjusted to that of the control free of any test compound (i.e., the pH value of the latter +0.2). In this respect, the evaluation criteria was set as follows: 0: the score of a test compound being equivalent to that of the control; 3: the score of a test compound being stronger than that of the control; and 5: the score of a test compound being extremely stronger than that of the control. Furthermore, to make the criterion for the evaluation more clearer, the following standards were set: 2.5: the initial-middle taste observed for γ-Glu-Val-Gly; and 3.0: the after taste thereof and the evaluation was carried out while 5 panelists were used for each evaluation test (n=5). In this connection, the intensity of the kokumi observed for γGlu-Val-Gly at a concentration of 0.001 g/dL corresponds to the intensity of the kokumi (3.0: the initial-middle taste; 3.0: the after taste) observed for γ-Glu-Cys-Gly (glutathione) at a concentration of 0.01 g/dL. The scoring was carried out using the linear-scale technique, in which each corresponding score was plotted on a straight line on which the scores equal to −5, 0 and +5 had been expressly specified. In addition, persons selected as panelists in these evaluation tests were persons who had been engaged in the development of a seasoning over a cumulative period of at least a half year, and who could so judge that the difference between γ-Glu-Cys-Gly and γ-Glu-Val-Gly, each of which was added to a solution having umami and salty taste, was about 10 times (this ability was confirmed at regular intervals). In this respect, the term "initial-middle taste" means the taste detected from 0 to 5 seconds after placing and maintaining each sample in each panelist's mouth, and the term "after taste" means that detected thereafter. The compound 8b used in these tests showed its kokumi-imparting activity over the wide range of the foregoing added concentrations, but the results observed at typical concentrations are shown in the following Table 2.

Moreover, Table 2 also shows the results obtained when γ-Glu-Val-Gly was evaluated according to the same procedures.

TABLE 2

| Comp. | Concn. (g/dL) | Intensity of Kokumi | | Comments for the Evaluation |
|---|---|---|---|---|
| | | Initial-Middle Taste | After Taste | |
| Control | — | 0 | 0 | |
| γ-Glu-Val-Gly | 0.001 | 2.5 | 3.0 | The kokumi is strengthened mainly with respect to the roundness, thickness and growth. |
| Comp. 8b | 0.0001 | 2.3 | 2.4 | The start of the initial taste of the compound is faster than that observed for γ-Glu-Val-Gly and the compound can impart kokumi rather approaching the initial taste. |
| | 0.0005 | 3.4 | 3.5 | The start of the initial taste of the compound is faster than that observed for γ-Glu-Val-Gly and the compound can impart kokumi rather approaching the initial taste. The compound can impart a strong UMAMI taste to the initial solution. It can impart thickness thereto. |

The foregoing results clearly indicate that the compound of the present invention shows an excellent kokumi-imparting activity, even at a very low concentration. This is quite useful from the industrial standpoint.

Example 27

Evaluation of Compounds According to the Present Invention for Kokumi-Imparting Activity in Case of Dried-Bonito Extract Compound 8b was inspected for the intensity of its kokumi-imparting activity according to the quantitative organoleptic evaluation test.

The quantitative organoleptic evaluation test was carried out according to the following procedures: The intensity of the kokumi-imparting activity of test compound was determined using a mixture obtained by diluting commercially available dried bonito extract (equivalent to a 50% broth of dried bonito) with hot water to a concentration of 20.0 g/dL, adding common salt (0.5 g/dL) to the diluted extract to give a solution of dried bonito extract and then incorporating a test compound, into the solution, in an amount ranging from 0.0001 to 0.0005 g/dL. The pH value of the samples used was adjusted to that of the control free of any test compound (i.e., the pH value of the latter +0.2). In this respect, the evaluation criteria was set as follows: 0: the score of a test compound being equivalent to that of the control; 3: the score of a test compound being stronger than that of the control; and 5: the score of a test compound being extremely stronger than that of the control. Further, to make the criterion for the evaluation more clearer, the following standards were set: 2.5: the initial-middle taste observed for γ-Glu-Val-Gly; and 3.0: the after taste thereof and the evaluation was carried out, while 5 panelists were used for each evaluation test (n=5). In this connection, the intensity of the kokumi observed for γ-Glu-Val-Gly at a concentration of 0.001 g/dL corresponds to the intensity of the kokumi (3.0: the initial-middle taste; 3.0: the after taste) observed for γ-Glu-Cys-Gly (glutathione) at a concentration of 0.01 g/dL. The scoring was carried out using the linear-scale technique, in which each corresponding score was plotted on a straight line on which the scores equal to −5, 0 and +5 had been expressly specified. In addition, the persons selected as panelists in these evaluation tests were persons who had been engaged in the development of seasonings over a cumulative period of at least a half year, and who could so judge that the difference between γ-Glu-Cys-Gly and γ-Glu-Val-Gly, each of which was added to a solution having a UMAMI taste and a salty taste, was about 10 times (this ability was confirmed at regular intervals). In this respect, the term "initial-middle taste" means the taste detected from 0 to 5 seconds after placing and maintaining each sample in each panelist's mouth, and the term "after taste" means that detected thereafter. The compound 8b used in these tests showed its kokumi-imparting activity over the wide range of the foregoing added concentrations, but the results observed at typical concentrations are shown in the following Table 3.

Moreover, Table 3 also shows the results obtained when γ-Glu-Val-Gly was evaluated according to the same procedures.

TABLE 3

| Comp. | Concn. (g/dL) | Intensity of Kokumi | | Comments for the Evaluation |
|---|---|---|---|---|
| | | Initial-Middle Taste | After Taste | |
| Control | — | 0 | 0 | |
| γ-Glu-Val-Gly | 0.001 | 2.5 | 3.0 | The fish meat taste of the dried bonito extract is strengthened. |
| Comp. 8b | 0.0001 | 2.3 | 2.5 | The start of the initial taste of the compound is faster than that observed for γ-Glu-Val-Gly and the compound can impart kokumi rather approaching the initial taste. The sour taste of the dried bonito extract becomes milder. |

TABLE 3-continued

| Comp. | Concn. (g/dL) | Intensity of Kokumi | | Comments for the Evaluation |
|---|---|---|---|---|
| | | Initial-Middle Taste | After Taste | |
| | 0.0005 | 3.5 | 3.7 | The start of the initial taste of the compound is faster than that observed for γ-Glu-Val-Gly and the compound can impart kokumi rather approaching the initial taste. The sour taste of the dried bonito extract becomes milder. The fish meat taste of the dried bonito extract is further strengthened. The compound can impart a strong UMAMI taste to the initial solution. |

With respect to even the dried bonito extract, it was found that the lanthionine derivative described herein can serve as an excellent kokumi-imparting agent which shows an excellent kokumi-imparting activity, even at a very low concentration. The dried bonito has widely been used in, for instance, MISO soup, soup for fine noodles, wheat vermicelli, and soup stock for vermicelli. More specifically, the compound described herein permits the improvement of the taste and palate of various foods which make use of dried bonito, at a low cost and in a very small amount. Accordingly, the compound described herein is useful from the industrial standpoint.

Example 28

Evaluation of Compounds for Kokumi-Imparting Activity in Case of Cow's Milk

Compound 8b was inspected for the intensity of its kokumi-imparting activity according to the quantitative organoleptic evaluation test.

The quantitative organoleptic evaluation test was carried out according to the following procedures: The intensity of the kokumi-imparting activity of the test compound was determined using a mixture obtained by adding, to the commercially available cow's milk (fat content: 3.6%), the test compound in an amount ranging from 0.0001 to 0.0005 g/dL. The pH value of the samples used was adjusted to that of the control free of any test compound (i.e., the pH value of the latter +0.2). In this respect, the evaluation criteria was set as follows: 0: the score of a test compound being equivalent to that of the control; 3: the score of a test compound being stronger than that of the control; and 5: the score of a test compound being extremely stronger than that of the control. Furthermore, to make the criterion for the evaluation more clearer, the following standards were set: 2.5: the initial-middle taste observed for γ-Glu-Val-Gly; and 3.0: the after taste thereof, and the evaluation was carried out, while 5 panelists were used for each evaluation test (n=5). In this connection, the intensity of the kokumi observed for γ-Glu-Val-Gly at a concentration of 0.001 g/dL corresponds to the intensity of the kokumi (3.0: the initial-middle taste; 3.0: the after taste) observed for γ-Glu-Cys-Gly (glutathione) at a concentration of 0.01 g/dL. The scoring was carried out using the linear-scale technique, in which each corresponding score was plotted on a straight line on which the scores equal to −5, 0 and +5 had been expressly specified. In addition, selected as panelists in these evaluation tests were persons who had been engaged in the development of seasonings over a cumulative period of at least a half year, and who could so judge that the difference between γ-Glu-Cys-Gly and γ-Glu-Val-Gly, each of which was added to a solution having umami and salty taste, was about 10 times (this ability was confirmed at regular intervals). In this respect, the term "initial-middle taste" means the taste detected during the term ranging from 0 to 5 seconds after keeping each sample in each panelist's mouth and the term "after taste" means that detected thereafter. The compound 8b used in these tests showed its kokumi-imparting activity over the wide range of the foregoing added concentrations, but the results observed at typical concentrations are shown in the following Table 4.

Moreover, Table 4 also shows the results obtained when γ-Glu-Val-Gly was evaluated according to the same procedures.

TABLE 4

| Comp. | Concn. (g/dL) | Intensity of Kokumi | | Comments for the Evaluation |
|---|---|---|---|---|
| | | Initial-Middle Taste | After Taste | |
| Control | — | 0 | 0 | |
| γ-Glu-Val-Gly | 0.001 | 2.5 | 3.0 | The thickness feeling of the cow's milk is strengthened. |
| Comp. 8b | 0.0001 | 2.4 | 2.3 | The start of the initial taste of the compound is faster than that observed for γ-Glu-Val-Gly and the compound can impart kokumi rather approaching the initial taste. |
| | 0.0005 | 3.5 | 3.5 | The start of the initial taste of the compound is faster than that observed for γ-Glu-Val-Gly and the compound can impart kokumi rather approaching the initial taste. The thickness feeling of the cow's milk is further strengthened. |

With respect to even the cow's milk, it was found that the lanthionine derivative can serve as an excellent kokumi-imparting agent which can show an excellent kokumi-imparting activity, even at a very low concentration. The cow's milk has widely been used in, for instance, ingredients for various foods, beverages, confectionery and fermented foods. More specifically, the compound of the present invention permits the improvement of the taste and palate of various foods which make use of cow's milk, at a low cost and in a very small amount. Accordingly, the compound described herein is quite useful from the industrial standpoint.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A compound having a structure represented by the following general formula (I), or an edible salt thereof:

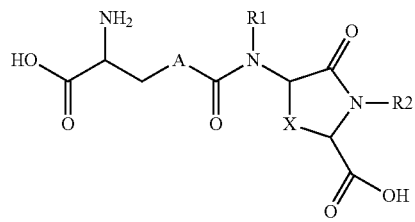

(I)

wherein R1 and R2 each independently represent a hydrogen atom or a lower alkyl group having 1 to 3 carbon atoms;

A represents a methylene group or an oxy group; and

X represents an alkylene group having 1 to 5 carbon atoms, provided that one of the methylene groups present in the alkylene group may be substituted with a thio group, a disulfide group, an oxy group, an imino group or an alkyl-imino group having 1 to 3 carbon atoms and that the alkylene group may further be substituted with 1 to 6 alkyl groups each having 1 to 3 carbon atoms.

2. The compound or an edible salt thereof as set forth in claim 1, wherein R1 and R2 in the general formula (I) represent hydrogen atoms.

3. The compound or an edible salt thereof as set forth in claim 1, wherein the group A in the general formula (I) represents a methylene group.

4. The compound or an edible salt thereof as set forth in claim 1, wherein the group X in the general formula (I) represents a trimethylene group in which one of the methylene group thereof is substituted with a thio group.

5. The compound or an edible salt thereof as set forth in claim 1, wherein it has a structure represented by the following general formula (IIa):

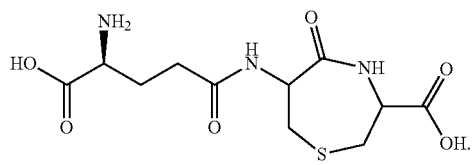

6. The compound or an edible salt thereof as set forth in claim 5, wherein it has a structure represented by the following general formula (8b):

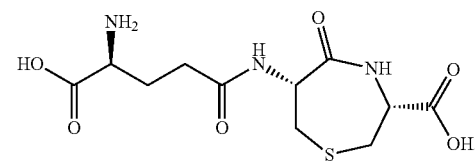

7. The compound or an edible salt thereof as set forth in claim 1, wherein the group X in the general formula (I) represents a tetramethylene group, one of the methylene group of which is substituted with a thio group, or a trimethylene group, which is substituted with an alkyl group having 1 to 3 carbon atoms and one of the methylene groups of which is replaced with a thio group.

8. The compound or an edible salt thereof as set forth in claim 1, wherein the group X in the general formula (I) represents a trimethylene group.

9. A food composition comprising a compound or an edible salt thereof as set forth in claim 1, in an amount ranging from 10 ppb to 99.9%.

10. A kokumi-imparting composition comprising a compound or an edible salt thereof as set forth in claim 1, as an effective component.

11. A compound having a structure represented by the following general formula (IA), or a chemically acceptable salt thereof:

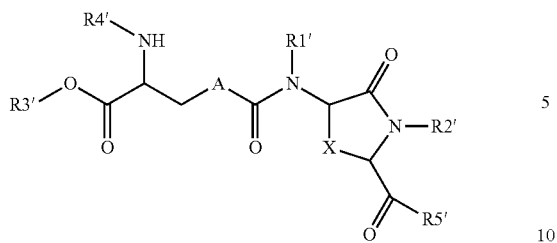

(IA)

wherein R1' and R2' each independently represent a hydrogen atom or an alkyl group having 1 to 3 carbon atoms;
- R3' represents a hydrogen atom, an alkyl group having 1 to 4 carbon atoms, a benzyl group, or a 9-fluorenylmethyl group;
- R4' represents a t-butoxycarbonyl group, a benzyloxycarbonyl group, or a 9-fluorenylmethyloxycarbonyl group;
- R5' represents a hydroxyl group, an alkoxy group having 1 to 4 carbon atoms, a benzyloxy group, an amino group ($-NH_2$) or an alkylamino group having 1 to 3 carbon atoms;
- A represents a methylene group or an oxy group; and
- X represents an alkylene group having 1 to 5 carbon atoms, provided that one of the methylene groups present in the alkylene group may be substituted with a thio group, a disulfide group, an oxy group, an imino group or an alkyl-imino group having 1 to 3 carbon atoms and that the alkylene group may further be substituted with 1 to 6 alkyl groups each having 1 to 3 carbon atoms.

\* \* \* \* \*